US012064665B2

(12) United States Patent
Jung et al.

(10) Patent No.: US 12,064,665 B2
(45) Date of Patent: Aug. 20, 2024

(54) ELECTRONIC APPARATUS AND OPERATING METHOD THEREOF

(71) Applicant: Samsung Electronics Co., Ltd., Gyeonggi-do (KR)

(72) Inventors: Jinyung Jung, Seoul (KR); Eunhye Lee, Seoul (KR); Dokshin Lim, Gyeonggi-do (KR); Kyunghoon Han, Seoul (KR)

(73) Assignee: Samsung Electronics Co., Ltd (KR)

( * ) Notice: Subject to any disclaimer, the term of this patent is extended or adjusted under 35 U.S.C. 154(b) by 238 days.

(21) Appl. No.: 17/509,433

(22) Filed: Oct. 25, 2021

(65) Prior Publication Data
US 2022/0040533 A1 Feb. 10, 2022

Related U.S. Application Data

(63) Continuation of application No. 15/611,382, filed on Jun. 1, 2017, now abandoned.

(30) Foreign Application Priority Data

Jun. 1, 2016 (KR) .................. 10-2016-0068245

(51) Int. Cl.
A61B 5/00 (2006.01)
A61B 5/024 (2006.01)
(Continued)

(52) U.S. Cl.
CPC ........ *A63B 24/0062* (2013.01); *A61B 5/0002* (2013.01); *A61B 5/0022* (2013.01);
(Continued)

(58) Field of Classification Search
USPC ....................................................... 600/301
See application file for complete search history.

(56) References Cited

U.S. PATENT DOCUMENTS 8,475,339 B2 7/2013 Hwang et al.
2009/0287103 A1 11/2009 Pillai
(Continued)

FOREIGN PATENT DOCUMENTS

JP 2003-085669 3/2003
JP 4485492 6/2010
(Continued)

OTHER PUBLICATIONS

KR Notice of Patent Grant dated Apr. 26, 2023 issued in counterpart application No. 10-2016-0068245, 5 pages.
(Continued)

*Primary Examiner* — Kesha Frisby
(74) *Attorney, Agent, or Firm* — The Farrell Law Firm, P.C.

(57) ABSTRACT

A method and an electronic apparatus is provided. A first UI indicating a start of an activity is displayed when first data indicating that the activity occurs is received from a first sensor. Information is displayed about a preset time or a preset intensity required for the activity to be converted into exercise. The preset time or the preset intensity is set based on user information related to a characteristic of a user. It is detected that the activity is maintained for at least one of the preset time or at the preset intensity. In response to the detecting that the activity is maintained, a second UI is displayed indicating a start of an exercise. A sensor is activated based on the start of the exercise and exercise history of the user. A function is executed for measuring exercise information by using second data received from the activated sensor.

20 Claims, 20 Drawing Sheets

(51) Int. Cl.
*A61B 5/11* (2006.01)
*A63B 24/00* (2006.01)
*A63B 71/06* (2006.01)
*G01C 22/00* (2006.01)
*A61B 5/01* (2006.01)
*A61B 5/0205* (2006.01)
*A61B 5/021* (2006.01)
*A61B 5/145* (2006.01)
*A61B 5/1455* (2006.01)
*A61B 5/318* (2021.01)

(52) U.S. Cl.
CPC ........ *A61B 5/02438* (2013.01); *A61B 5/1118* (2013.01); *A61B 5/112* (2013.01); *A61B 5/1123* (2013.01); *A63B 24/0075* (2013.01); *A63B 71/0622* (2013.01); *G01C 22/006* (2013.01); *A61B 5/01* (2013.01); *A61B 5/0205* (2013.01); *A61B 5/021* (2013.01); *A61B 5/14532* (2013.01); *A61B 5/14551* (2013.01); *A61B 5/318* (2021.01); *A61B 5/6824* (2013.01); *A61B 2505/09* (2013.01); *A61B 2562/0219* (2013.01); *A63B 2024/0068* (2013.01); *A63B 2071/0663* (2013.01); *A63B 2220/17* (2013.01); *A63B 2220/20* (2013.01); *A63B 2220/30* (2013.01); *A63B 2220/62* (2013.01); *A63B 2220/836* (2013.01); *A63B 2225/50* (2013.01); *A63B 2230/04* (2013.01); *A63B 2230/06* (2013.01); *A63B 2230/207* (2013.01); *A63B 2230/30* (2013.01); *A63B 2230/65* (2013.01); *A63B 2230/75* (2013.01)

(56) References Cited

U.S. PATENT DOCUMENTS

| | | |
|---|---|---|
| 2010/0292050 A1 | 11/2010 | DiBenedetto et al. |
| 2012/0119911 A1 | 5/2012 | Jeon |
| 2015/0057944 A1 | 2/2015 | White et al. |
| 2015/0265160 A1 | 9/2015 | Kato |
| 2016/0058336 A1 | 3/2016 | Blahnik et al. |
| 2017/0046108 A1 | 2/2017 | Kang et al. |

FOREIGN PATENT DOCUMENTS

| | | |
|---|---|---|
| JP | 2013-009969 | 1/2013 |
| KR | 10-2012-0130306 | 11/2012 |
| KR | 10-2015-0029479 | 3/2015 |
| KR | 10-2016-0045874 | 4/2016 |
| KR | 2017-0020085 | 2/2017 |
| WO | WO 2013/109762 | 7/2013 |
| WO | WO 2016/036582 | 3/2016 |

OTHER PUBLICATIONS

Korean Office Action dated Oct. 26, 2022 issued in counterpart application No. 10-2016-0068245, 12 pages.
European Search Report dated Jan. 31, 2023 issued in counterpart application No. 17807021.5-1113, 9 pages.
https://help.fitbit.com/articles/en US/Help_article/SmartTrack-Faqs, Mar. 28, 2017.
Indian Examination Report dated Oct. 7, 2020 issued in counterpart application No. 201827045751, 7 pages.
European Search Report dated May 6, 2019 issued in counterpart application No. 17807021.5-1115, 9 pages.
International Search Report dated Aug. 11, 2017 issued in counterpart application No. PCT/KR2017/005715, 10 pages.

ELECTRONIC APPARATUS AND OPERATING METHOD THEREOF

PRIORITY

This application is a Continuation Application of U.S. application Ser. No. 15/611,382, which was filed in the U.S. Patent and Trademark Office on Jun. 1, 2017, which claims priority under 35 U.S.C. § 119(a) to Korean Patent Application Ser. No. 10-2016-0068245, which was filed in the Korean Intellectual Property Office on Jun. 1, 2016, the entire content of which is incorporated herein by reference.

BACKGROUND

1. Field of the Disclosure

The present disclosure relates, generally, to an electronic apparatus and an operating method thereof.

2. Description of the Related Art

Electronic apparatuses can be carried in a pocket of a user or worn on their wrist, head arm, etc., and may include various sensors (e.g., an accelerometer and a biometric sensor) to measure user exercise information. The exercise information may be a result of measuring the amount of activity performed by the user for a certain period of time.

The electronic apparatuses may detect a user input to start and end an exercise, and to measure exercise information. For example, electronic apparatuses may measure an amount of activity from a start time of an exercise to end time of an exercise. Sometimes, however, the electronic apparatuses may not record the activity of the user as exercise information.

SUMMARY

The present disclosure has been made to address at least the disadvantages described above and to provide at least the advantages described below. Accordingly, an aspect of the present disclosure provides an electronic apparatus and a method of use thereof that enables an activity of the user to be automatically recorded as exercise information without any special manipulation, and that automatically outputs the activity of the user and exercise information for the user's reorganization without any special manipulation.

In accordance with an aspect of the present disclosure, an electronic apparatus is provided that includes a display, a sensor group including a first sensor and a plurality of second sensors, and at least one processor connected to the display and the sensor group. The at least one processor is configured to display, via the display, a first user interface (UI) indicating a start of an activity when first data indicating that the activity of the electronic apparatus occurs is received from the first sensor. The at least one processor is also configured to display, via the display, information about a preset time or a preset intensity required for the activity to be converted into exercise. The preset time or the preset intensity is set based on user information related to a characteristic of a user. The at least one processor is further configured to detect that the activity is maintained for at least one of the preset time or at the preset intensity, and, in response to the detecting, display a second UI indicating a start of the exercise via the display. Additionally, the at least one processor is configured to activate at least one sensor from among the plurality of second sensors based on the start of the exercise and exercise history of the user, and execute a function for measuring exercise information by using second data received from the activated at least one sensor.

In accordance with an aspect of the present disclosure, a method of an electronic apparatus including a sensor group is provided. A first UI indicating a start of an activity is displayed when first data indicating that the activity of the electronic apparatus occurs is received from a first sensor of the sensor group. Information is displayed about a preset time or a preset intensity required for the activity to be converted into exercise. The preset time or the preset intensity is set based on user information related to a characteristic of a user. It is detected that the activity is maintained for at least one of the preset time or at the preset intensity. In response to the detecting that the activity is maintained for at least one of the preset time or at the preset intensity, a second UI is displayed indicating a start of an exercise. At least one sensor from among a plurality of second sensors in the sensor group is activated based on the start of the exercise and exercise history of the user. A function is executed for measuring exercise information by using second data received from the activated at least one sensor.

In accordance with an aspect of the present disclosure, a non-transitory computer-readable recording medium is provided that stores a program in a memory of an electronic device. The program when executed displays a first UI indicating a start of an activity when first data indicating that the activity of the electronic apparatus occurs is received from a first sensor among a sensor group in the electronic device. The program displays information about a preset time or a preset intensity required for the activity to be converted into exercise. The preset time or the preset intensity is set based on user information related to a characteristic of a user. The program detects that the activity is maintained for at least one of the preset time or at the preset intensity. In response to the detecting, the program displays a second UI indicating a start of the exercise. The program activates at least one sensor from among a plurality of second sensors in the sensor group based on the start of the exercise and exercise history of the user. The program executes a function for measuring exercise information by using second data received from the activated at least one sensor.

BRIEF DESCRIPTION OF THE DRAWINGS

The above and other aspects, features and advantages of certain exemplary embodiments of the present invention will be more apparent from the following detailed description taken in conjunction with the accompanying drawings, in which.

DETAILED DESCRIPTION

Figure 1A:
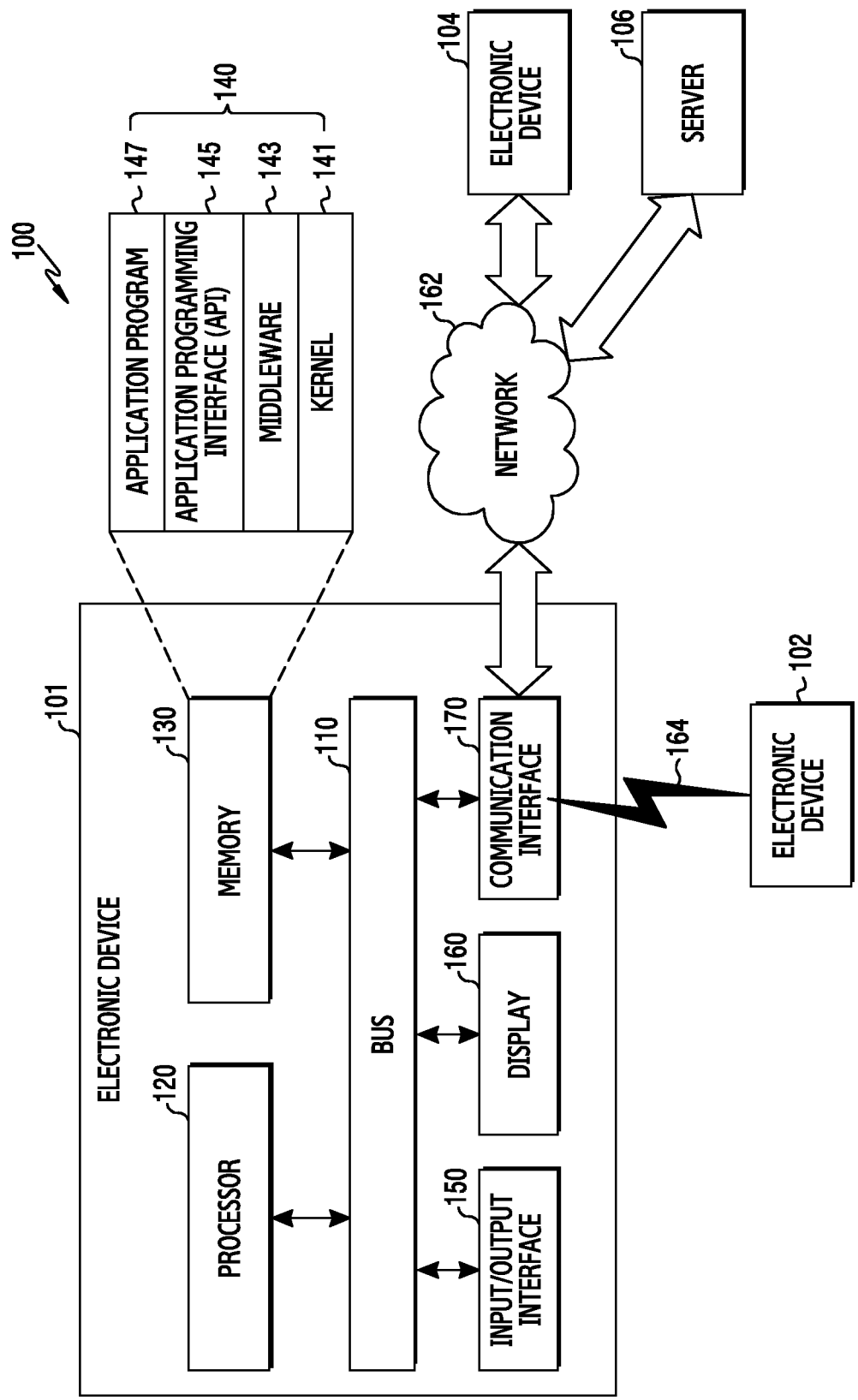
FIG. 1A is a diagram of an electronic apparatus in a network environment, according to an embodiment of the present disclosure.

Embodiments of the present disclosure will be described herein below with reference to the accompanying drawings. However, the embodiments of the present disclosure are not limited to the specific embodiments and should be construed as including all modifications, changes, equivalent devices and methods, and/or alternative embodiments of the present disclosure. In the description of the drawings, similar reference numerals are used for similar elements.

The terms "have," "may have," "include," and "may include" as used herein indicate the presence of corresponding features (for example, elements such as numerical values, functions, operations, or parts), and do not preclude the presence of additional features.

The terms "A or B," "at least one of A or/and B," or "one or more of A or/and B" as used herein include all possible combinations of items enumerated with them. For example, "A or B," "at least one of A and B," or "at least one of A or B" means (1) including at least one A, (2) including at least one B, or (3) including both at least one A and at least one B.

The terms such as "first" and "second" as used herein may modify various elements regardless of an order and/or importance of the corresponding elements, and do not limit the corresponding elements. These terms may be used for the purpose of distinguishing one element from another element. For example, a first user device and a second user device may indicate different user devices regardless of the order or importance. For example, a first element may be referred to as a second element without departing from the scope the present invention, and similarly, a second element may be referred to as a first element. It will be understood that, when an element (for example, a first element) is "(operatively or communicatively) coupled with/to" or "connected to" another element (for example, a second element), the element may be directly coupled with/to another element, and there may be an intervening element (for example, a third element) between the element and another element. To the contrary, it will be understood that, when an element (for example, a first element) is "directly coupled with/to" or "directly connected to" another element (for example, a second element), there is no intervening element (for example, a third element) between the element and another element.

The expression "configured to (or set to)" as used herein may be used interchangeably with "suitable for," "having the capacity to," "designed to," "adapted to," "made to," or "capable of" according to a context. The term "configured to (set to)" does not necessarily mean "specifically designed to" in a hardware level. Instead, the expression "apparatus configured to . . . " may mean that the apparatus is "capable of . . . " along with other devices or parts in a certain context. For example, "a processor configured to (set to) perform A, B, and C" may mean a dedicated processor (e.g., an embedded processor) for performing a corresponding operation, or a generic-purpose processor (e.g., a CPU or an application processor) capable of performing a corresponding operation by executing one or more software programs stored in a memory device.

The terms used in describing the various embodiments of the present disclosure are for the purpose of describing particular embodiments and are not intended to limit the present disclosure. As used herein, the singular forms are intended to include the plural forms as well, unless the context clearly indicates otherwise. All of the terms used herein including technical or scientific terms have the same meanings as those generally understood by an ordinary skilled person in the related art unless they are defined otherwise. The terms defined in a generally used dictionary should be interpreted as having the same or similar meanings as the contextual meanings of the relevant technology and should not be interpreted as having ideal or exaggerated meanings unless they are clearly defined herein. According to circumstances, even the terms defined in this disclosure should not be interpreted as excluding the embodiments of the present disclosure.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present invention may include at least one of an application-specific integrated circuit (ASIC) chip, a field-programmable gate arrays (FPGA), and a programmable-logic device for performing operations which has been known or are to be developed hereinafter.

An electronic device according to the present disclosure may include at least one of, for example, a smart phone, a tablet personal computer (PC), a mobile phone, a video phone, an electronic book reader (e-book reader), a desktop PC, a laptop PC, a netbook computer, a workstation, a server, a personal digital assistant (PDA), a portable multimedia player (PMP), a MPEG-1 audio layer-3 (MP3) player, a mobile medical device, a camera, and a wearable device. The wearable device may include at least one of an accessory type (e.g., a watch, a ring, a bracelet, an anklet, a necklace, a glasses, a contact lens, or a head-mounted device (HMD)), a fabric or clothing integrated type (e.g., an electronic clothing), a body-mounted type (e.g., a skin pad, or tattoo), and a bio-implantable type (e.g., an implantable circuit).

The electronic device may be a home appliance. The home appliance may include at least one of, for example, a television, a digital video disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™) a game console (e.g., Xbox™ and PlayStation™), an electronic dictionary, an electronic key, a camcorder, and an electronic photo frame.

The electronic device may include at least one of various medical devices (e.g., various portable medical measuring devices (a blood glucose monitoring device, a heart rate monitoring device, a blood pressure measuring device, a body temperature measuring device, etc.), a magnetic resonance angiography (MRA), a magnetic resonance imaging (MRI), a computed tomography (CT) machine, and an ultrasonic machine), a navigation device, a global positioning system (GPS) receiver, an event data recorder (EDR), a flight data recorder (FDR), a vehicle infotainment device, an electronic device for a ship (e.g., a navigation device for a ship, and a gyro-compass), avionics, security devices, an automotive head unit, a robot for home or industry, an automatic teller machine (ATM) in banks, point of sales (POS) devices in a shop, or an Internet of things (IoT) device (e.g., a light bulb, various sensors, electric or gas meter, a sprinkler device, a fire alarm, a thermostat, a streetlamp, a toaster, a sporting goods, a hot water tank, a heater, a boiler, etc.).

The electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device may be a combination of one or more of the aforementioned various devices. The electronic device may also be a flexible device further, the electronic device is not limited to the aforementioned devices, and may include an electronic device according to the development of new technology.

Hereinafter, an electronic device will be described with reference to the accompanying drawings. In the present disclosure, the term "user" may indicate a person using an electronic device or a device an artificial intelligence electronic device) using an electronic device.

Referring to FIG. 1A, an electronic device 101 resides in a network 100 and can include a bus 110, a processor 120, a memory 130, an input/output (110) interface 150, a display 160, and a communication interface 170. The electronic device 101 can omit at least one of the components or further include another component.

The bus 110 can include a circuit for connecting the components 110 to 170 and delivering communication signals (e.g., control messages or data) therebetween. The processor 120 can include one or more of a central processing unit, an application processor, and a communication processor (CP). The processor 120 can perform an operation or data processing on control and/or communication of at least another component of the electronic device 101.

The processor 120 may provide an exercise information measurement function. For example, the processor 120 may detect an activity with a regular pattern (e.g., user's movement with a regular pattern) based on sensor information collected by at least one designated sensor and may determine whether the detected activity is converted/changed/ transitions into (or associated with) an exercise. For example, when it is determined that the user performs a continuous activity, the processor 120 may determine that the detected activity is converted into exercise.

The memory 130 can include a volatile and/or nonvolatile memory. The memory 130 can store commands or data relating to at least another component of the electronic device 101.

The memory 130 may store information necessary to measure exercise information, which may include at least one of a threshold for determining a meaningful activity with a pattern, a threshold for determining whether a detected activity is converted into exercise, and a threshold for determining whether an activity determined as exercise has stopped or finished.

The memory 130 can store software and/or a program 140. The program 140 can include a kernel 141, middleware 143, an application programming interface (API) 145, and/ or an application program (or "application") 147.

At least part of the kernel 141, the middleware 143, or the API 145 can be called an operating system (OS). The kernel 141 can control or manage system resources (e.g., the bus 110, the processor 120, or the memory 130) used for performing operations or functions implemented by the other programs (e.g., the middleware 134, the API 145, or the application 147). Additionally, the kernel 141 can provide an interface for controlling or managing system resources by accessing an individual component of the electronic device 101 from the middleware 143, the API 145, or the application 147.

The middleware 143 can serve as an intermediary role for exchanging data between the API 145 or the application 147 and the kernel 141 through communication. Additionally, the middleware 132 can process one or more job requests received from the application 147, based on their priority. For example, the middleware 143 can assign a priority for using a system resource (e.g., the bus 110, the processor 120, or the memory 130) of the electronic device 101 to at least one of the applications 147, and process the one or more job requests.

The API 145, as an interface through which the application 147 controls a function provided from the kernel 141 or the middleware 143, can include at least one interface or function (e.g., an instruction) for file control, window control, image processing, or character control.

The I/O interface 150 may recognize a user's input, and may be a touch input unit. In addition, the I/O interface 150 may be an input/output interface including an output unit. The input/output interface 150 may serve as an interface for delivering a command or data which is inputted from the user or another external device to the other element(s) of the electronic device 101. In addition, the input/output interface 150 may output a command or data which is received from the other element(s) of the electronic device 101 to the user or another external device.

The display 160 can include a liquid crystal display (LCD), a light emitting diode (LED) display, an organic light emitting diode (OLED) display, a microelectromechanical systems (MFMS) display, or an electronic paper display. The display 160 can display various contents (e.g., texts, images, videos, icons, and/or symbols) to the user. The display 160 can include a touch screen and receive touch, gesture, proximity, or hovering inputs by using an electronic pen or a user's body part.

The communication interface 170 can set a communication between the electronic device 101 and a first external electronic device 102, a second external electronic device 104, or a server 106. For example, the communication interface 170 can communicate with the second external electronic device 104 or the server 106 over the network 162 through wireless communication or wired communication.

The wireless communication can be one of long term evolution (LTE), LTE-advanced (LTE-A), code division multiple access (CDMA), wideband CDMA (WCDMA), universal mobile telecommunications system (UMTS), wireless broadband (WiBro), and global system for mobile communications (GSM), as a cellular communication protocol. The wireless communication may include short-range communication 164. The short-range communication 164 may be conducted by at least one of wireless-fidelity (WiFi) ®, bluetooth (BT)®, BT low energy (BLE), Zigbee®, near field communication (NFC), magnetic secure transmission, radio frequency (RE), and body area network (BAN). The wireless communication can include global navigation satellite system (GNSS). The GNSS can include global positioning system (GPS), global navigation satellite system (Glonass), BeiDou navigation satellite system (BeiDou), or Galileo (the European global satellite-based navigation system). Hereafter, GPS can be interchangeably used with the GNSS.

The wired communication can include at least one of universal serial bus (USB), high definition multimedia interface (MAID, recommended standard 232 (RS-232), power line communications, and plain old telephone service (POTS). The network 162 can include at least one of telecommunications networks such as computer network (e.g., LAN or WAN), Internet, and telephone network.

Each of the first and second external electronic devices 102 and 104 can be the same or different type of the electronic device 101. All or part of operations executed in the electronic device 101 can be executed by the electronic device 102 or 104 or the server 106. When the electronic device 101 is to perform a function or service automatically or at the request, instead of performing the function or the service by the electronic device 101 or additionally, the electronic device 101 can request at least part of a function relating thereto from the electronic device 102 or 104, or the server 106. The electronic device 102 or 104, or the server 106 can perform the requested function or an additional function and deliver its result to the electronic device 101. The electronic device 101 can provide the requested function or service by processing the received result as is or by using cloud computing, distributed computing, or client-server computing techniques.

Figure 1B:
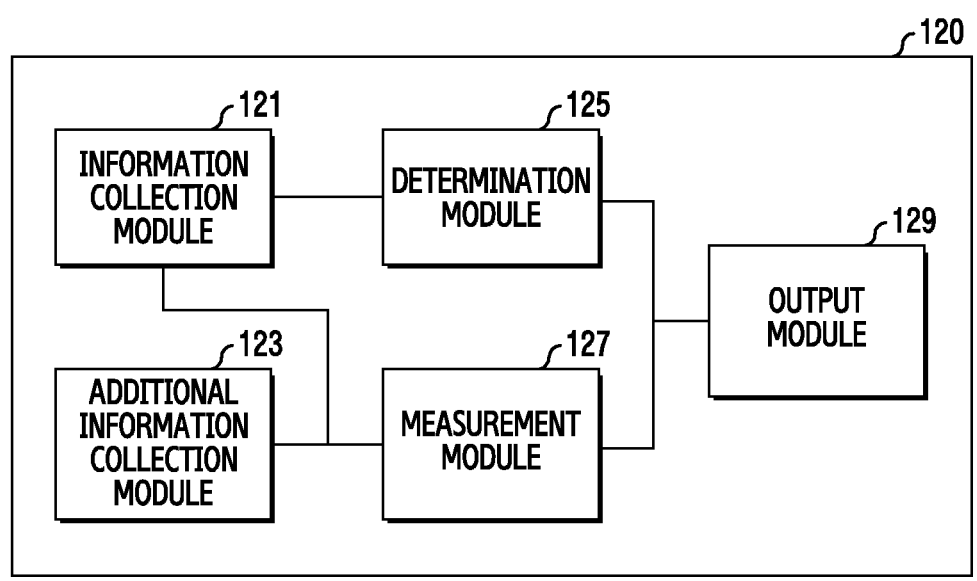
FIG. 1B is a block diagram of a processor, according to an embodiment of the present disclosure.

FIG. 1B is a block diagram illustrating the processor 120, according to an embodiment of the present disclosure.

The processor 120 may include an information collection module 121, an additional information collection module 123, a determination module 125, a measurement module 127, and an output module 129.

The information collection module 121 may collect sensor information associated with a movement of the electronic apparatus 101 through at least one designated sensor. For example, the information collection module 121 may collect sensor information from at least one sensor among an accelerometer, a passometer, and a pedometer. The information collection module 121 may be activated to collect sensor information during a mode of determining an activity state or exercise state of a user carrying the electronic apparatus 101. The activity state may refer to a state in which the user is moving in a regular pattern, and the exercise state may refer to a state in which the user is able to obtain exercise effects through a continuous activity. When the information collection module 121 collects sensor information associated with a movement, the information collection module 121 may provide the collected sensor information to the determination module 125 and the measurement module 127.

The additional information collection module 123 may collect additional sensor information associated with an activity of the user through at least one additional sensor of the electronic apparatus 101, e.g., from at least one of a biometric sensor and a position measurement sensor. The biometric sensor may include at least one of a heart rate sensor, a blood pressure sensor, an electrocardiogram (ECG) sensor, a skin moisture sensor, and an oxygen saturation sensor. The additional information collection module 123 may be activated to collect additional sensor information in a mode of measuring an exercise result of the user carrying the electronic apparatus 101 (e.g., exercise mode). The additional information collection module 123 may switch to a deactivated state in a mode of determining an activity of the user not carrying the electronic apparatus 101. When the additional information collection module 123 collects additional sensor information, the additional information collection module 123 may provide the collected additional sensor information the measurement module 127.

The determination module 125 may determine whether a detected activity is converted (or changed) into exercise based on at least part of the sensor information collected by the information collection module 121. For example, the determination module 125 may determine a pattern (e.g., step counts, a pace, and moving speed) of a movement of the electronic apparatus 101 using the sensor information and may determine an activity of the user carrying the electronic apparatus 101 based on the determined pattern. The determination module 125 may determine at least one activity among a walking activity, a running activity, a cycle-using activity, a sports equipment-using activity, and a vehicle-using activity.

When a movement with a pattern is determined as an activity of the user, the determination module 125 may determine whether exercise effects are obtained by monitoring the activity of the user. For example, when the determined activity of the user is maintained for a preset time or at a preset intensity, the determination module 125 may determine that the activity with a pattern is converted into exercise. When it is determined that the activity is converted into exercise, the determination module 125 may also determine whether the converted exercise is stopped or finished.

The measurement module 127 may measure exercise information based on the acquired sensor information.

When the mode of determining the activity state or exercise state is operating, the measurement module 127 may measure exercise information based on sensor information acquired by the information collection module 121. The measurement module 127 may measure, as exercise information, information (e.g., exercise type, exercise time, calorie consumption, moving speed, and average speed) associated with a movement continuing for a certain period of time (e.g., from activity start time to exercise end time).

When the mode of measuring the exercise result is operating, the measurement module 127 may measure exercise information based on sensor information acquired by the information collection module 121 and the additional information collection module 123. The measurement module 127 may measure, as exercise information, information (e.g., exercise type, exercise time, calorie consumption, moving speed, and average speed) associated with a movement continuing for a certain period of time (e.g., from activity start time to exercise end time), information (e.g., moving path) associated with a position, and biometric information (e.g., heart rate).

The output module 129 may output information associated with the mode of determining the activity state or exercise state and the mode of measuring the exercise result. When an activity of the user associated with a movement of the electronic apparatus 101 is detected by the determination module 125, the output module 129 may output activity start information. When a conversion of the activity of the user into exercise is detected by the determination module 125, the output module 129 may output an exercise start notification.

When exercise information is measured by the measurement module 127, the output module 129 may output an exercise result.

Figure 2:
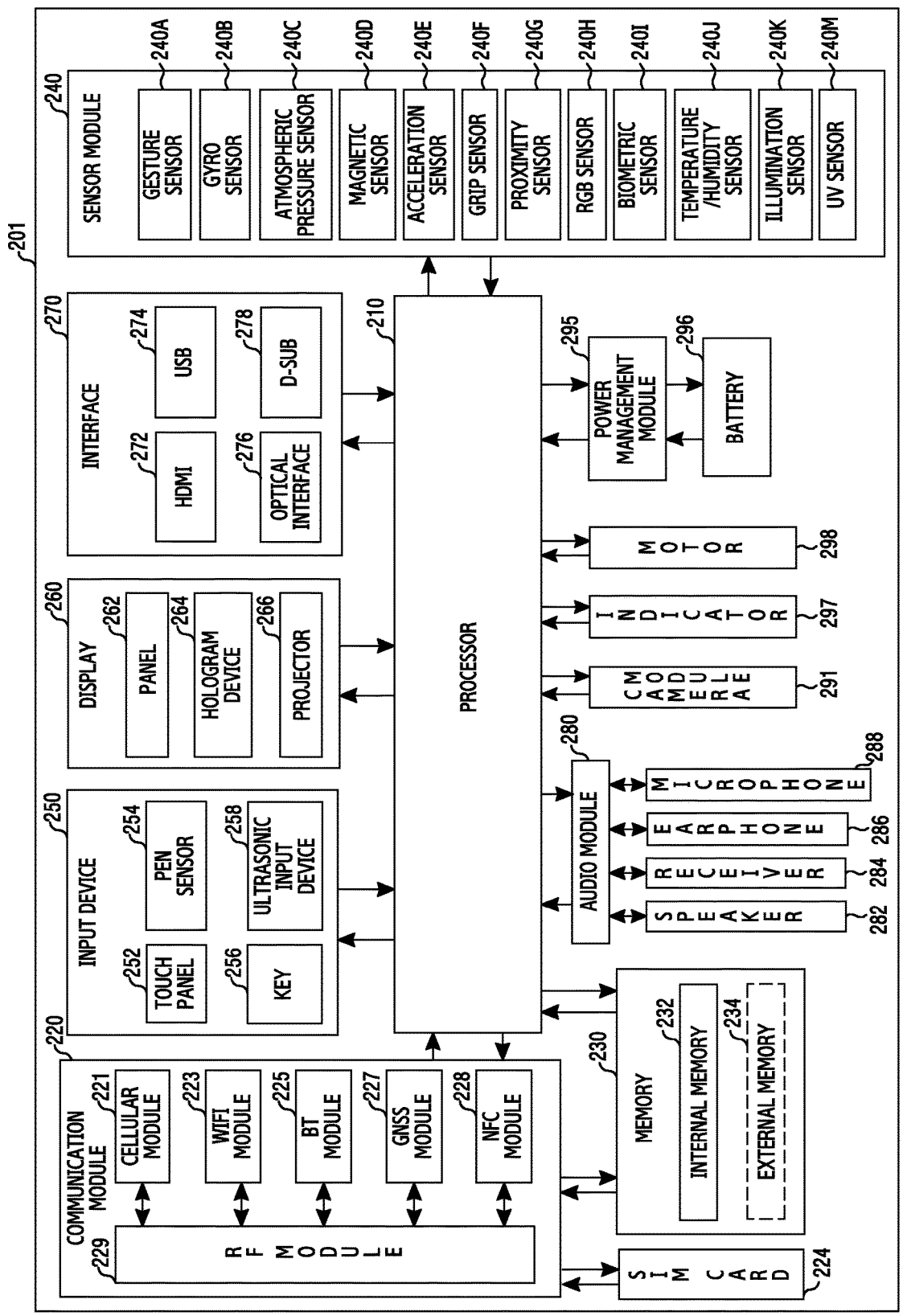
FIG. 2 is a block diagram of an electronic apparatus, according to an embodiment of the present disclosure.

FIG. 2 is a block diagram illustrating an electronic device 201, according to an embodiment of the present disclosure. The electronic device 201 may include all or a portion of the electronic device 101 illustrated in FIG. 1A. The electronic device 201 may include one or more processors (e.g., AP) 210, a communication module 220, a subscriber identification module (SIM) 224, a memory 230, a sensor module 240, an input unit 250, a display 260, an interface 270, an audio module 280, a camera module 291, a power management module 295, a battery 296, an indicator 297, or a motor 298.

The processor 210 may drive an OS or an application to control a plurality of hardware or software elements connected to the processor 210, and perform various data processes including multimedia data and operations. The processor 210 may be implemented as a system on chip (SoC). The processor 210 may further include at least one of a graphic processing unit (GPU) or image signal processor. The processor 210 may be implemented to include at least a portion (e.g., the cellular module 221) of the above-described elements. Also, the processor 210 may store data received from at least one of other elements or generated by at least one of other elements in a non-volatile memory.

The communication module 220 may perform data transmission/reception in communication between the electronic device 201 and other electronic devices connected via a network. The communication module 220 may include a cellular module 221, a Wi-Fi module 223, a BT module 225, a GPS module 227, an INK module 228, and an RF module 229.

The cellular module 221 may provide voice communication, image communication, a short message service, or an Internet service, etc. via a communication network (e.g., LTE, CDMA, WCDMA, UMTS, WiBro, or GSM, etc.). Also, the cellular module 221 may perform discrimination and authentication of an electronic device within a communication network using the SIM 224, The cellular module 221 may perform at least a portion of functions that may be provided by the processor 210. The cellular module 221 may include a CP. Also, the cellular module 221 may be implemented as an SoC. Though elements such as the cellular module 221 (e.g., a communication processor), the memory 230, or the power management module 295, etc. are illustrated as elements separated from the processor 210 in FIG. 2, the processor 210 may be implemented to include at least a portion (e.g., the cellular module 221) of the above-described elements.

Each of the Wi-Fi module 223, the BT module 225, the GPS module 227, or the NFC module 228 may include a processor for processing data transmitted/received via a relevant module. Though the cellular module 221, the Wi-Fi module 223, the BT module 225, the GPS module 227, or the NFC module 228 are illustrated as separate blocks in FIG. 2, at least a portion (e.g., two or more elements) of the cellular module 221, the Wi-Fi module 223, the BT module 225, the GPS module 227, or the NFC module 228 may be included in one integrated circuit (IC) or an IC package. At least a portion (e.g., a communication processor corresponding to the cellular module 221 and a Wi-Fi processor corresponding to the Wi-Fi module 223) of processors corresponding to each of the cellular module 221, the Wi-Fi module 223, the BT module 225, the GPS module 227, or the NFC module 228 may be implemented as one SoC.

The RF module 229 may perform transmission/reception of data, e.g., transmission/reception of an RF signal. The RF module 229 may include a transceiver, a power amp module (PAM), a frequency filter, or a low noise amplifier (LNA), etc. Also, the RF module 229 may further include a part for transmitting/receiving an electromagnetic wave on a free space in wireless communication, e.g., a conductor or a conducting line, etc. Though FIG. 2 illustrates the cellular module 221, the Wi-Fi module 223, the BT module 225, the GPS module 227, and the NEC module 228 share one RE module 229, at least one of the cellular module 221, the Wi-Fi module 223, the BT module 225, the GPS module 227, or the NEC module 228 may perform transmission/reception of an RE signal via a separate RE module.

The SIM 224 may be a card including a SIM, and may be inserted into a slot formed in a specific position of the electronic device. The SIM 224 may include unique identity information (e.g., integrated circuit card identifier (ICCID)) or subscriber information (e.g., international mobile subscriber identity (IMSI)).

The memory 230 may include a built-in memory 232 or an external memory 234, The built-in memory 232 may include at least one of a volatile memory (e.g., dynamic RAM (DRAM), static RAM (SRAM), synchronous dynamic RAM (SDRAM)) and a non-volatile memory (e.g., one time programmable ROM (OTPROM), programmable ROM (PROM), erasable and programmable ROM (EPROM), electrically erasable and programmable ROM (EEPROM), mask ROM, flash ROM, NAND flash memory, NOR flash memory, etc.).

The built-in memory 232 may be a solid state drive (SSD). The external memory 234 may further include a flash drive, e.g., compact flash (CO, secure digital (SD), micro secure digital (Micro-SD), mini secure digital (Mini-SD), extreme digital (xD), or a memory stick. The external memory 234 may be functionally connected with the electronic device 201 via various interfaces. The electronic device 201 may further include a storage device (or a storage medium) such as a hard drive.

The sensor module 240 may measure a physical quantity or detect an operation state of the electronic device 201, and convert the measured or detected information to an electric signal. The sensor module 240 may include at least one of a gesture sensor 240A, a gyro sensor 240B, an atmospheric pressure sensor 240C, a magnetic sensor 240D, an acceleration sensor 240E, a grip sensor 240F, a proximity sensor 240G, a color sensor 240H (e.g., RGB (red, green, blue) sensor), a living body sensor 240I, a temperature/humidity sensor 240J, an illuminance sensor 240K, or an ultra violet (UV) sensor 240M. Additionally or alternatively, the sensor module 240 may include an e-nose sensor, an electromyography (EMG) sensor, an electroencephalogram (EEG) sensor, an electrocardiogram (ECG) sensor, an infrared (IR) sensor, an iris sensor, or a fingerprint sensor, etc. The sensor module 240 may further include a control circuit for controlling at least one sensor belonging thereto.

The input unit 250 may include a touch panel 252, a (digital) pen sensor 254, a key 256, or an ultrasonic input unit 258. The touch panel 252 may recognize a touch input using at least one of capacitive, resistive, infrared, or ultrasonic methods. Also, the touch panel 252 may further include a control circuit. A capacitive touch panel may perform detection by a physical contact or proximity recognition. The touch panel 252 may further include a tactile layer. In this case, the touch panel 252 may provide a tactile reaction to a user.

The (digital) pen sensor 254 may be implemented using a method which is the same as or similar to receiving a user's touch input, or using a separate sheet for detection. The key 256 may include a physical button, an optical key or keypad. The ultrasonic input unit 258 is a unit for recognizing data by detecting a sound wave using a microphone 288 in the electronic device 201 via an input tool generating an ultrasonic signal, and enables wireless recognition. The electronic device 201 may receive a user input from an external device (e.g., a computer or a server) connected to the communication module 220 using the communication module 220.

The display 260 may include a panel 262, a hologram device 264, or a projector 266. The panel 262 may be an LCD, or an active-matrix organic light-emitting diode (AM-OLED), etc. The panel 262 may be implemented such that it is flexible, transparent, or wearable. The panel 262 may be configured as one module together with the touch panel 252. The hologram device 264 may show a three-dimensional image in the air using interferences of light. The projector 266 may project light onto a screen to display an image. The screen may be positioned inside or outside the electronic device 201. The display 260 may further include a control circuit for controlling the panel 262, the hologram device 264, or the projector 266.

The interface 270 may include an HDMI 272, a USB 274, an optical interface 276, or a d-subminiature (D-sub) 278. The interface 270 may be included in the communication interface 160 illustrated in FIG. 1A. Additionally or alternatively, the interface 270 may include a mobile high-definition link (MHL) interface, a secure digital (SD) card/multi-media card (MMC) interface, or an infrared data association (IrDA) standard interface.

The audio module 280 may convert a sound and an electric signal in dual directions. At least a partial element of the audio module 280 may be included in the I/O interface 140 illustrated in FIG. 1A. The audio module 280 may process sound information input or output via, for example, a speaker 282, a receiver 284, an earphone 286, or the microphone 288, etc.

The camera module 291 is a device that may shoot a still image and a moving picture.

The camera module 291 may include one or more image sensors (e.g., a front sensor or a rear sensor), a lens, an image signal processor (ISP), or a flash (e.g., an LED or xenon lamp).

The power management module 295 may manage power of the electronic device 201. Though not shown, the power management module 295 may include a power management integrated circuit (PMIC), a charger integrated circuit (IC), and/or a battery gauge.

The PMIC may be mounted inside an integrated circuit or a SoC semiconductor. A charging method may be classified into a wired charging method and a wireless charging method. The charging IC may charge a battery and prevent introduction of an overvoltage or an overcurrent from a charger. The charging IC may include a charging IC for at least one of the wired charging method and the wireless charging method. The wireless charging method may be a magnetic resonance method, a magnetic induction method, or an electromagnetic wave method, etc., and may additionally include an additional circuit for wireless charging, e.g., a circuit such as a coil loop, a resonance circuit, or a rectifier, etc.

The battery gauge may measure a remaining power of the battery 296, a voltage, a current, or a temperature while charging. The battery 296 may store or generate electricity, and supply power to the electronic device 201 using the stored or generated electricity. The battery 296 may include a rechargeable battery or a solar battery.

The indicator 297 may display a specific state of the electronic device 201 or a portion thereof (e.g., the processor 210), e.g., a booting state, a message state, or a charging state, etc. The motor 298 may convert an electric signal to mechanical vibration. Though not shown, the electronic device 201 may include a processor (e.g., a GPU) for supporting a mobile TV. The processor for supporting the mobile TV may process media data corresponding to standards, for example, such as digital multimedia broadcasting (DMB), digital video broadcasting (DVB), or a media flow, etc.

The aforementioned elements of the electronic device may be constituted by one or more components, and the name of the corresponding element may vary with a type of electronic device. The electronic device may include at least one of the aforementioned elements. Some elements may be omitted or other additional elements may be further included in the electronic device. Further, some of the components of the electronic device may be combined to form a single entity, and thus, may equivalently execute functions of the corresponding elements prior to the combination.

Figure 3:
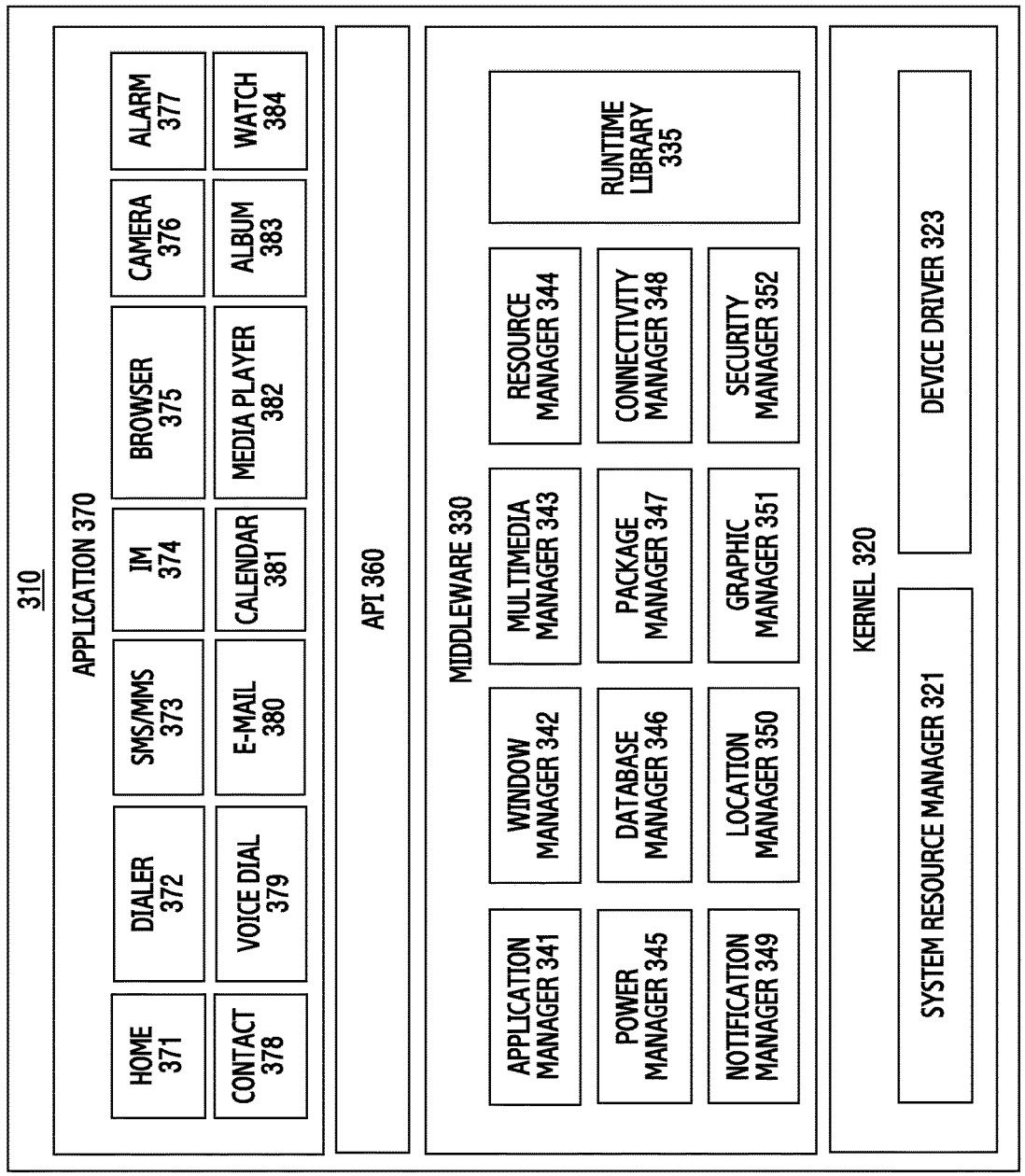
FIG. 3 is a block diagram of a program module, according to an embodiment of the present disclosure.

FIG. 3 is a block diagram of a program module 310, according to an embodiment of the present disclosure.

The program module 310 may include an OS for controlling resources related to the electronic device and/or various applications (e.g., the application 147) executed in the OS. The operating system may be Android™, iOS™, Windows™, Symbian™, Tizen™, Bada™, or the like.

The programming module 310 may include a kernel 320, middleware 330, an API 360, and/or applications 370. At least some of the program module 310 may be preloaded in the electronic device or downloaded from the server.

The kernel 320 may include a system resource manager 331 or a device driver 333. The system resource manager 331 may control, allocate, or collect the system resources. The system resource manager 331 may include a process management unit, a memory management unit, or a file system management unit. The device driver 333 may include a display driver, a camera driver, a BT driver, a shared-memory driver, a USB driver, a keypad driver, a WiFi driver, an audio driver, or an inter-process communication (IPC) driver.

The middleware 330 may provide a function required by the applications 370 in common or provide various functions to the applications 370 through the API 360 so that the applications 370 can efficiently use limited system resources within the electronic device. The middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses to add new functions through a programming language while the application 370 is executed. The runtime library 335 may perform input/output management, memory management, or a function for an arithmetic function.

The application manager 341 may manage a life cycle of at least one of the applications 370. The window manager 342 may manage GUI resources used by a screen.

The multimedia manager 343 may grasp formats required for the reproduction of various media files, and may perform an encoding or decoding of the media file by using a codec suitable for the corresponding format. The resource manager 344 may manage resources such as a source code, a memory, and a storage space of at least one of the applications 370.

The power manager 345 may operate together with a basic input/output system (BIOS) to manage a battery or power and may provide power information required for the operation of the electronic device. The database manager 346 may generate, search for, or change a database to be used by at least one of the applications 370. The package manager 347 may manage the installation or the updating of applications distributed in the form of package file.

The connectivity manager 348 may manage wireless connection of WiFi or BT. The notification manager 349 can display or notify of an event such as an arrival message, promise, proximity notification, and the like in such a way that does not disturb a user. The location manager 350 may manage location information of the electronic device. The graphic manager 351 may manage graphic effects to be provided to a user and user interfaces related to the graphic effects. The security manager 352 may provide all security functions required for system security or user authentication. When the electronic device (e.g., electronic device 100) has a call function, the middleware 330 may further include a telephony manager for managing a voice call function or a video call function of the electronic device.

The middleware 330 may include a middleware module for forming a combination of various functions of the aforementioned components. The middleware 330 may provide modules specialized according to types of operating systems in order to provide differentiated functions. Further, the middleware 330 may dynamically remove some of the existing components or add new components.

The API 360 is a set of API programming functions, and a different configuration thereof may be provided according to an OS. For example, Android™ or iOS™ may provide one API set per platform, and Tizen™ may provide two or more API sets per platform.

The applications 370 (may include one or more applications which can provide functions such as a home application 371, a dialer application 372, an SMS/MMS application 373, an instant message application (1M) 374, a browser application 375, a camera application 376, an alarm application 377, a contacts application 378, a voice dialer application 379, an email application 380, a calendar application 381, a media player application 382, an album application 383, a clock application 384, a health care application (e.g., one that measures exercise quantity or blood glucose level), or environment information (e.g., atmospheric pressure, humidity, or temperature information).

The applications 370 may include an information exchange application supporting information exchange between an electronic device and an external electronic device. The information exchange application may include a notification relay application for transferring predetermined information to an external electronic device or a device management application for managing an external electronic device.

The notification relay application may include a function of transferring, to the external electronic device, notification information generated from other applications of the electronic device 100 (for example, an SMS/MMS application, an e-mail application, a health management application, or an environmental information application). Further, the notification relay application may receive notification information from a control device and provide the received notification information to the user. The device management application may manage (e.g., install, delete, or update a function for at least a part of the external electronic device communicating with the electronic device (e.g., turning on/off the external electronic device itself (or some elements thereof) or adjusting brightness (or resolution) of a display), applications executed in the external electronic device, or services provided from the external electronic device (e.g., a telephone call service or a message service).

The applications 370 may include an application (e.g., health management application) designated according to attributes of the external electronic device (e.g., attributes of the electronic device such as the type of electronic device which corresponds to a mobile medical device). The applications 370 may include an application received from the external electronic devices (e.g., a server or an electronic device). The applications 370 may include a preloaded application or a third party application which can be downloaded from the server. The names of the components of the program module 310 according to the embodiment illustrated in FIG. 3 may vary according to the type of OS.

At least some of the programming module 310 may be implemented by software, firmware, hardware, or a combination of two or more thereof. At least some of the programming module 310 may be implemented (e.g., executed) by the processor (e.g., an application). At least some of the programming module 310 may include a module, program, routine, sets of instructions, or process for performing one or more functions.

At least some of the devices (for example, modules or functions thereof) or the method (for example, operations) may be implemented by a command stored in a non-transitory computer-readable storage medium in a programming module form. The instruction, when executed by a processor, may cause the one or more processors to execute the function corresponding to the instruction. The non-transitory computer-readable storage medium may be the memory 130.

The non-transitory computer readable recoding medium may include a hard disk, a floppy disk, magnetic media (e.g., a magnetic tape), optical media (e.g., a compact disc read only memory (CD-ROM) and a DVD), magneto-optical media (e.g., a floptical disk), a hardware device (e.g., a read only memory (ROM), a Random Access Memory (RAM), a flash memory), and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

The programming module may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

An electronic apparatus may include a sensor; and a processor configured to be electrically connected to the sensor. According to one exemplary embodiment, the processor may be configured to: generate information indicating an activity start when first data indicating that an activity of the electronic apparatus occurs is received from the sensor; and generate information indicating an exercise start when second data indicating that the activity is converted into exercise is received from the sensor.

The processor may be configured to measure exercise information by detecting an exercise information measurement event after generating the information indicating the exercise start.

The electronic apparatus may further include a display configured to be electrically connected to the processor, and the processor may be configured to: display a user interface displaying an activity of a user on the display; and display the information indicating the activity start on a first area of the user interface based on the first data.

The electronic apparatus may further include a display configured to be electrically connected to the processor, and the processor may be configured to: display a user interface displaying an activity of a user on the display; and display the information indicating the exercise start in a second area, which is larger than a first area, of the user interface based on the second data.

The electronic apparatus may further include an additional sensor, and the processor may be configured to receive additional data from the additional sensor to measure the exercise information.

The electronic apparatus may further include a display configured to be electrically, connected to the processor, and the processor may be configured to display the measured exercise information on the display.

The processor may be configured to change a threshold for measuring the exercise information based on a characteristic of a user.

The processor may be configured to generate information indicating an exercise stoppage when third data indicating an activity stoppage is received from the sensor, after generating the information indicating the activity start.

The processor may be configured to measure exercise information based on data received from the sensor when fourth data indicating an activity end is received from the sensor, after generating the information indicating the activity start.

The processor may be configured to output guide information based on the measured exercise information and a preset target exercise amount.

Figure 4:
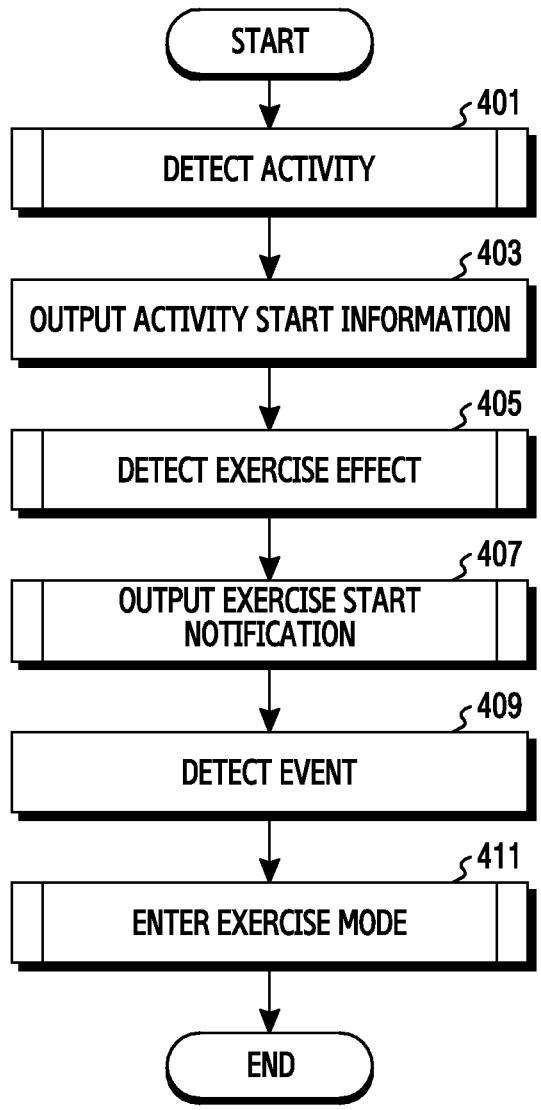
FIG. 4 is a flowchart of a method used by the electronic apparatus for processing activity information, according to an embodiment of the present disclosure.
Figure 5A:
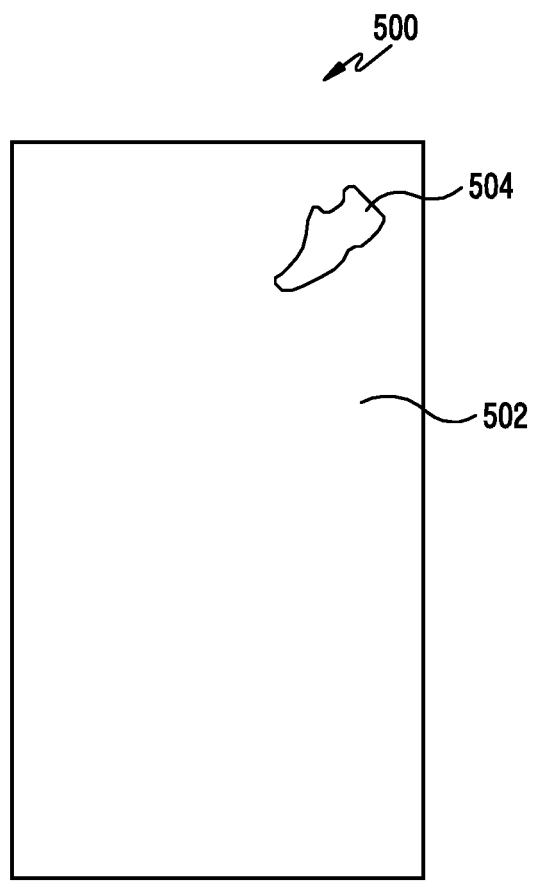
FIGS. 5A and 5B are diagrams of activity start information, according to an embodiment of the present disclosure.
Figure 5B:
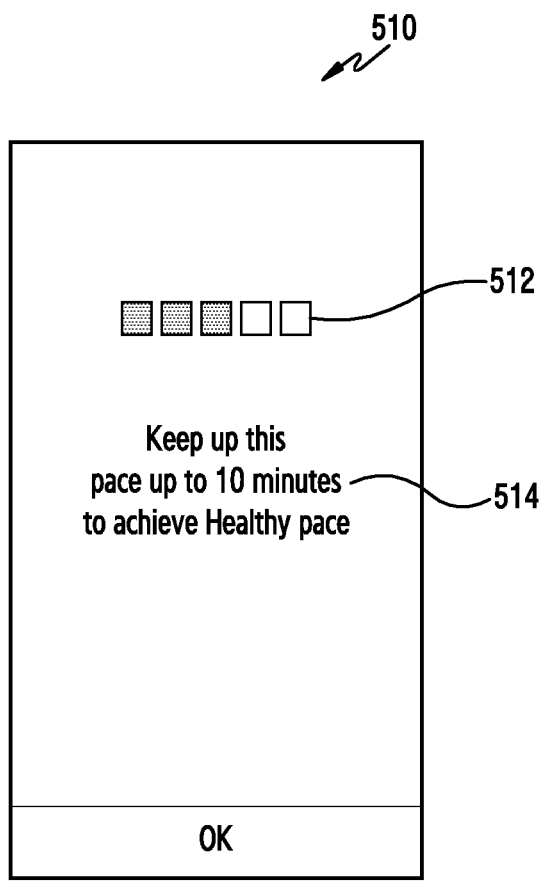
Figure 6:
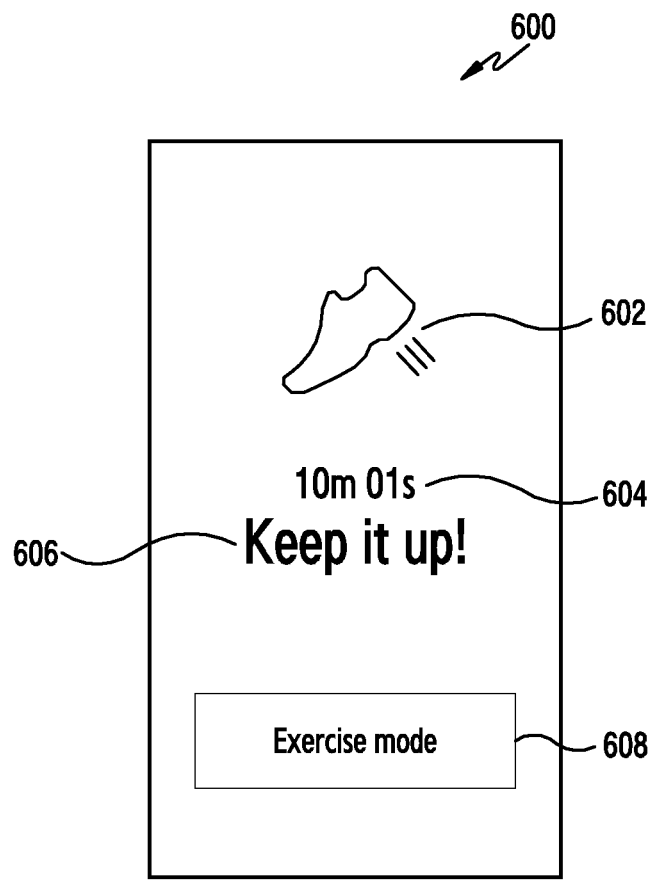
FIG. 6 is a diagram of an exercise start notification, according to an embodiment of the present disclosure.

The sensor may include a pedometer, and the additional sensor may include a biometric sensor FIG. 4 is a flowchart of a method used by the electronic apparatus 101 for processing activity information, according to an embodiment of the present disclosure. FIGS. 5A, 5B, and 6 are diagrams of an activity information processing operation, according to an embodiment of the present disclosure. Hereinafter, the electronic apparatus 101 may refer to the processor 120 of the electronic apparatus 101.

Referring to FIG. 4, in operation 401, the electronic apparatus 101 may detect an activity of a user (e.g., a user carrying the electronic apparatus 101) associated with a movement of the electronic apparatus 101. For example, the electronic apparatus 101 may detect a regular pattern of a movement of the electronic apparatus 101 based on sensor information continuously or periodically collected by a designated sensor (e.g., an accelerometer, a passometer, and a pedometer). The pattern may include step counts, a pace, moving speed, etc. The electronic apparatus 101 may detect, using the detected pattern, an activity of the user corresponding to at least one of a walking activity, a running activity, a cycle-using activity, a sports equipment-using activity (e.g., elliptical and rowing machines), and a vehicle-using activity. The electronic apparatus 101 may detect that the movement of the user is a walking activity when detecting a pattern satisfying a condition (e.g., step counts (e.g., 100 steps/min) or moving speed (e.g., 5 km/h)). The electronic apparatus 101 may detect that the movement of the user is a running activity when detecting a pattern satisfying a condition (e.g., step counts (e.g., 150 steps/min) or moving speed (e.g., 10 km/h)).

In operation 403, the electronic apparatus 101 may output activity start information indicating that the activity starts when detecting the activity of the user.

As illustrated in FIG. 5A, the electronic apparatus 101 may output (the output is indicated by reference number 500) visual activity start information 504 on a portion of a display 502. The visual activity start information may include a text, an image, an icon, etc. The electronic apparatus 101 may detect the activity with the display deactivated (e.g., with no screen output). The electronic apparatus 101 may activate at least part of the deactivated display to output the activity start information. In addition, the electronic apparatus 101 may detect the activity with the display activated (e.g., with a preset screen displayed). The electronic apparatus 101 may output the activity start information to overlap with at least part of the output screen. The electronic apparatus 101 may output tactile activity start information (vibrations). The electronic apparatus 101 may output audio activity start information (a notification sound).

The electronic apparatus 101 may output the activity start information as information representing the detected activity. For example, when detecting a walking activity, the electronic apparatus 101 may output at least one of an icon, vibrations, and a notification sound representing the walking activity as activity start information. When detecting a running activity, the electronic apparatus 101 may output at least one of an icon, vibrations, and a notification sound representing the running activity as activity start information.

After the activity start information is output, the electronic apparatus 101 may output information indicating a current activity state. For example, as illustrated in FIG. 5B, the electronic apparatus 101 may output 510 a state of maintenance (progress) of an activity 512 and time to the conversion of an activity into exercise 514. The information indicating the activity state may be output when an input on the output activity start information is detected.

In operation 405, the electronic apparatus 101 may detect an exercise effect of the detected activity. The electronic apparatus 101 may determine whether the detected activity is converted into exercise by monitoring the duration of the detected activity or the intensity of the detected activity. When the detected activity is maintained for a preset time (e.g., 10 minutes) or at a preset intensity, the electronic apparatus 101 may determine that the exercise effect on the user is detected.

In operation 407, the electronic apparatus 101 may output an exercise start notification when the exercise effect is detected. The electronic apparatus 101 may output a visual exercise start notification on the entire display while the exercise is progressing (or is maintained). The electronic apparatus 101 may output the exercise start notification including predetermined information. For example, as illustrated in FIG. 6, the electronic apparatus 101 may output the exercise start notification including an exercise type 602, exercise effect duration 604, an encouragement message 606 to increase an exercise effect, and a menu 608 to enter an exercise mode. The exercise mode may be a mode of measuring and recording an exercise result. The electronic apparatus 101 may output a tactile exercise start notification and an audio exercise start notification.

In operation 409, the electronic apparatus 101 may detect an event associated with an entry to the exercise mode. For example, when a preset input is detected with the exercise start notification output, the electronic apparatus 101 may determine that the event is detected. The preset input may include an input of selecting (or touching) the menu to enter the exercise mode. When exercise maintained for a preset time (e.g., 10 minutes) is detected with the exercise start notification output, the electronic apparatus 101 may determine that the event is detected. When a preset gesture input or voice instruction input is detected with the exercise start notification output, the electronic apparatus 101 may determine that the event is detected.

In operation 411, the electronic apparatus 101 may enter the exercise mode when the event is detected. When the electronic apparatus 101 enters the exercise mode, the electronic apparatus 101 may run an exercise application for exercise result measurement. In addition, when the electronic apparatus 101 enters the exercise mode, the electronic apparatus 101 may operate an additional sensor, which may include at least one of a biometric sensor and a position measurement sensor, FIG. 7 is a flowchart of a method used by the electronic apparatus 101 for detecting an activity, according to an embodiment of the present disclosure.

The procedure for detecting the activity is the same as operation 401 illustrated in FIG. 4.

Figure 7:
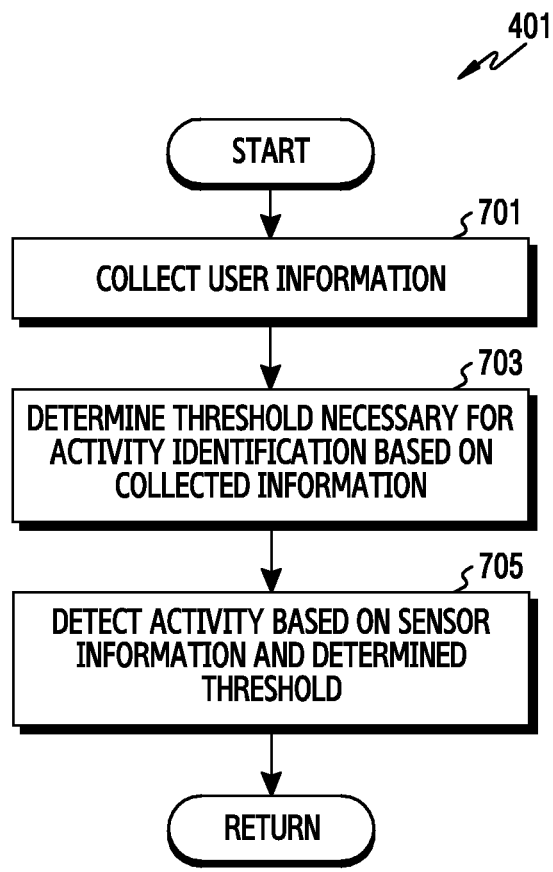
FIG. 7 is a flowchart of a method used by the electronic apparatus for detecting an activity, according to an embodiment of the present disclosure.

Referring to FIG. 7, the electronic apparatus 101 may determine a pattern of a movement of the electronic apparatus 101 using a pattern threshold. The electronic apparatus 101 may use different pattern thresholds depending on user characteristics (e.g., age, gender, and body types).

In operation 701, the electronic apparatus 101 may collect user information to determine user characteristics. The electronic apparatus 101 may collect, as user information, at least one of profile information (e.g., name and age) on the user, activity history information (e.g., weekly activity amount and favorite activities), activity pattern information (e.g., activity period, inactivity period, and sleeping period), a biometric information measurement history (e.g., information on heart rate during activity), and a medical history. The electronic apparatus 101 may acquire the user information from the electronic apparatus 101 or an external electronic apparatus connected via communication.

In operation 703, when a characteristic of the user is determined, the electronic apparatus 101 may determine a pattern threshold corresponding to the determined characteristic. The electronic apparatus 101 may determine a first pattern threshold for pattern determination when a male user is identified. The first pattern threshold may be defined based on a pace, step counts, speed, and distance as shown in Table 1 below. The electronic apparatus 101 may determine a second pattern threshold for pattern determination when a female user is identified. The second pattern threshold may be defined based on a pace, step counts, speed, and distance as shown in Table 2 below.

TABLE 1

| Activity type | Pace | Step counts | Speed | Distance |
| --- | --- | --- | --- | --- |
| Walking activity | 40 cm | 100 steps/min | 5 km/h | 60 m/min |
| Running activity | 50 cm | 150 steps/min | 10 km/h | 100 m/min |

TABLE 2

| Activity type | Pace | Step counts | Speed | Distance |
| --- | --- | --- | --- | --- |
| Walking activity | 30 cm | 80 steps/min | 3 km/h | 40 m/min |
| Running activity | 40 cm | 100 steps/min | 8 km/h | 80 m/min |

In operation 705, the electronic apparatus 101 may detect an activity based on sensor information and the determined pattern threshold. The electronic apparatus 101 may detect an activity corresponding to a movement of the user carrying the electronic apparatus 101 by comparing the determined pattern threshold with the sensor information. With the first pattern threshold (e.g., the pattern threshold for a male user) determined, when a pace of 40 cm is detected, the electronic apparatus 101 may detect a walking activity. Further, with the second pattern threshold (e.g., the pattern threshold for a female user) determined, when a pace of 40 cm is detected, the electronic apparatus 101 may detect a running activity.

Figure 8:
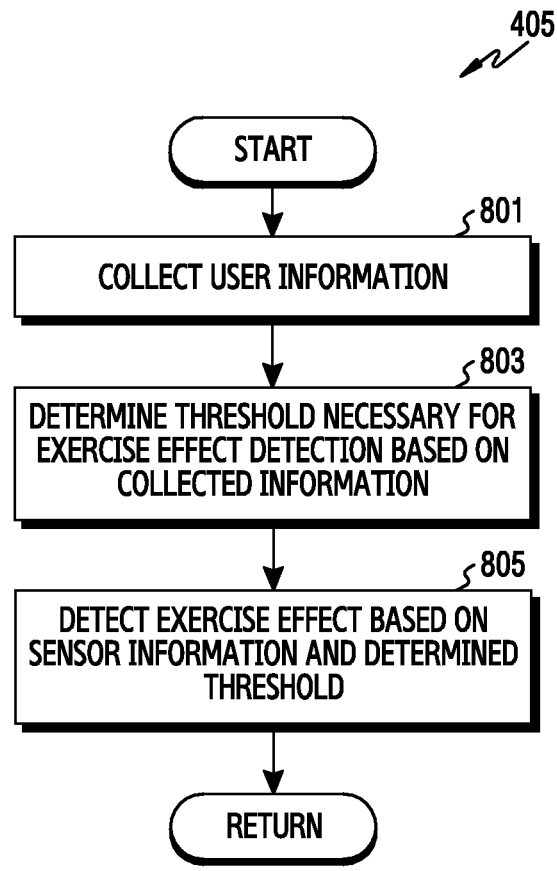
FIG. 8 is a flowchart of a method used by the electronic apparatus for detecting an exercise effect, according to an embodiment of the present disclosure.

FIG. 8 is a flowchart of a method used by the electronic apparatus 101 for detecting an exercise effect, according to an embodiment of the present disclosure.

The procedure for detecting the exercise effect may be the same as operation 405 illustrated in FIG. 4.

Referring to FIG. 8, the electronic apparatus 101 may determine whether an exercise effect occurs using an effect threshold. For example, the electronic apparatus 101 may use different effect thresholds depending on user characteristics (e.g., age, gender, and body types).

In operation 801, the electronic apparatus 101 may collect user information to determine user characteristics. The electronic apparatus 101 may collect, as user information, at least one of profile information on the user, activity history information, activity pattern information, a biometric information measurement history, and a medical hi story.

In operation 803, when a characteristic of the user is determined, the electronic apparatus 101 may determine an effect threshold corresponding to the determined characteristic. The electronic apparatus 101 may determine a first effect threshold for exercise effect detection when a male user is identified. The first effect threshold may be defined based on activity duration as shown in Table 3 below. The electronic apparatus 101 may determine a second effect threshold for exercise effect detection when a female user is identified. The second effect threshold may be defined based on activity duration as shown in Table 4 below.

TABLE 3

| Activity type | Activity duration |
| --- | --- |
| Walking activity | 10 min |
| Running activity | 8 min |

TABLE 4

| Activity type | Activity duration |
| --- | --- |
| Walking activity | 8 min |
| Running activity | 5 min |

In operation 805, the electronic apparatus 101 may detect an exercise effect based on sensor information and the determined effect threshold. When sensor information satisfying the determined effect threshold is collected, the electronic apparatus 101 may determine that an exercise effect is obtained by an activity of the user carrying the electronic apparatus 101.

Figure 9:
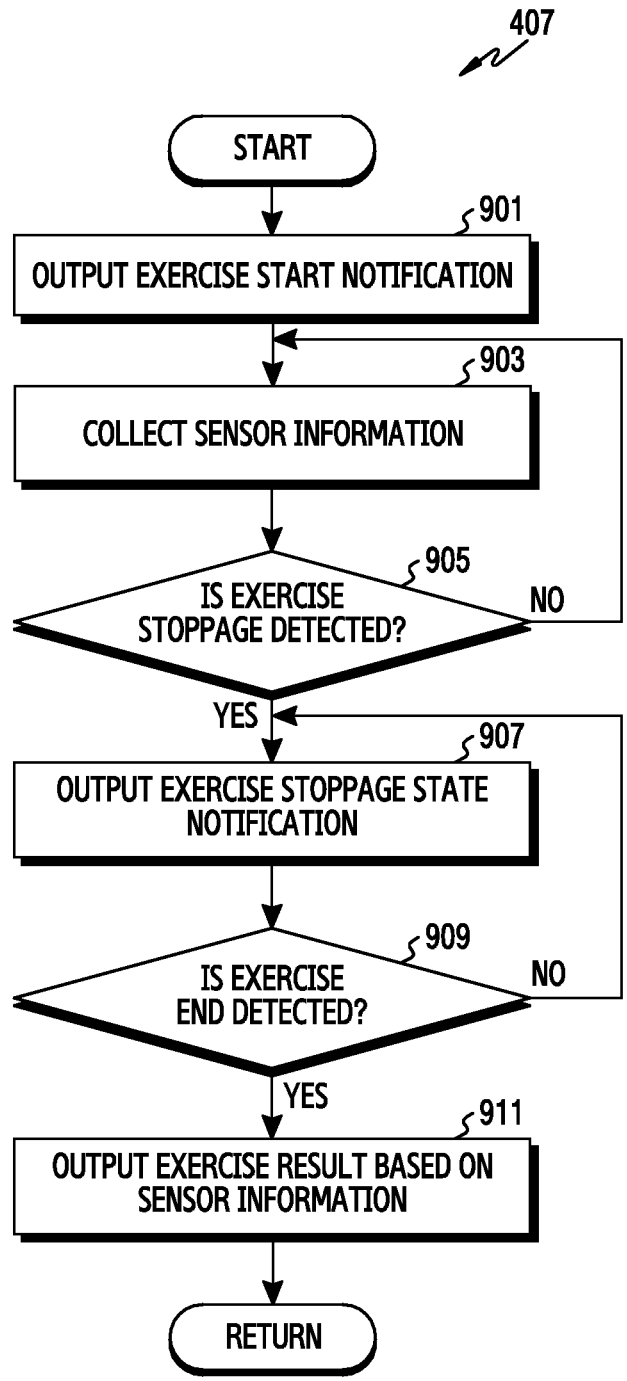
FIG. 9 is a flowchart of a method used by the electronic apparatus for outputting an exercise start notification, according to an embodiment of the present disclosure.
Figure 10A:
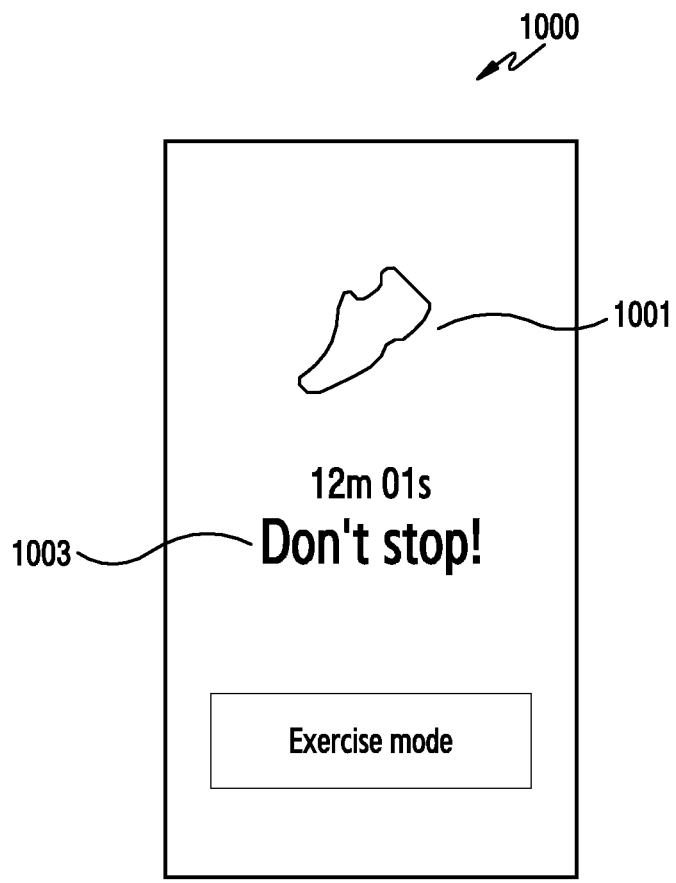
FIGS. 10A and 10B are diagrams of an operation for outputting an exercise start notification, according to an embodiment of the present disclosure.
Figure 10B:
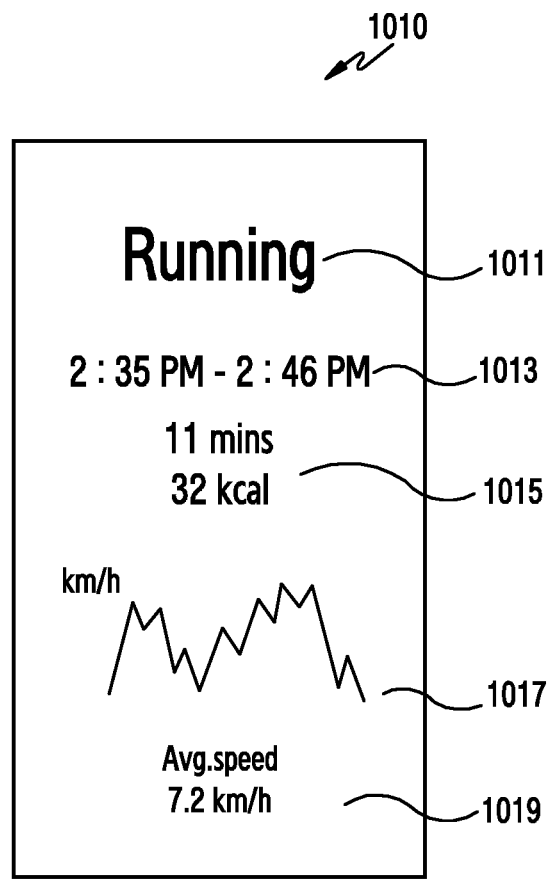

FIG. 9 is a flowchart of a method used by the electronic apparatus 101 for outputting an exercise start notification, according to an embodiment of the present disclosure. FIGS. 10A and 10B are diagrams of an operation of outputting an exercise start notification, according to an embodiment of the present disclosure.

The procedure for outputting the exercise start notification may be the same as operation 407 illustrated in FIG. 4.

Referring to FIG. 9, in operation 901, the electronic apparatus 101 may output the exercise start notification. The electronic apparatus 101 may report that the activity of the user carrying the electronic apparatus 101 is maintained.

In operation 903, the electronic apparatus 101 may collect sensor information from at least one designated sensor. The designated sensor may be a sensor that collects sensor information associated with movement information on the electronic apparatus 101. The electronic apparatus 101 may collect sensor information through at least one sensor among an accelerometer, a passometer, and a pedometer.

In operation 905, the electronic apparatus 101 may determine whether the exercise is stopped. A stoppage of the exercise may be a state in which the activity of the user carrying the electronic apparatus 101 is temporarily inactive. For instance, a stoppage of the exercise may be a state in which the user stops walking or running for a preset time (e.g., 1 minute) after starting a walking activity or running activity.

When a stoppage of the exercise is not detected in operation 905, the electronic apparatus 101 may perform an operation associated with operation 901 or operation 903.

When the stoppage of the exercise is detected in operation 905, the electronic apparatus 101 may output an exercise stoppage state notification in operation 907. For example, the electronic apparatus 101 may output the exercise stoppage state notification using visual, tactile, and audio notifications. For instance, as illustrated in FIG. 10A, the electronic apparatus 101 may output 1000 an exercise stoppage state notification including information 1001 indicating an exercise stoppage state and a message 1003 to lead to an exercise start.

In operation 909, the electronic apparatus 101 may determine whether the exercise is finished. The end of the exercise may be a state in which no additional activity is performed after stopping the activity of the user carrying the electronic apparatus 101 (or outputting the exercise stoppage state notification). The end of the exercise may be a state in which a stoppage of the activity is maintained for a preset time (e.g., 5 minutes) or a state in which a user input to indicate the end of the exercise is detected with the stoppage of the activity, detected.

When an end of the exercise is not detected in operation 909, the electronic apparatus 101 may perform an operation of detecting whether the exercise is finished. For example, the electronic apparatus 101 may perform an operation associated with operation 903 or operation 907.

When the end of the exercise is detected in operation 909, the electronic apparatus 101 may output an exercise result using sensor information in operation 911. For example, the electronic apparatus 101 may output an exercise result using sensor information collected from activity start time to exercise end time. For example, as illustrated in FIG. 10B, the exercise result 1010 may include predetermined information (e.g., exercise type 1011, exercise time 1013, calorie consumption 1015, moving speed 1017, and average speed 1019) that may be measured with sensor information associated with a movement.

Figure 11:
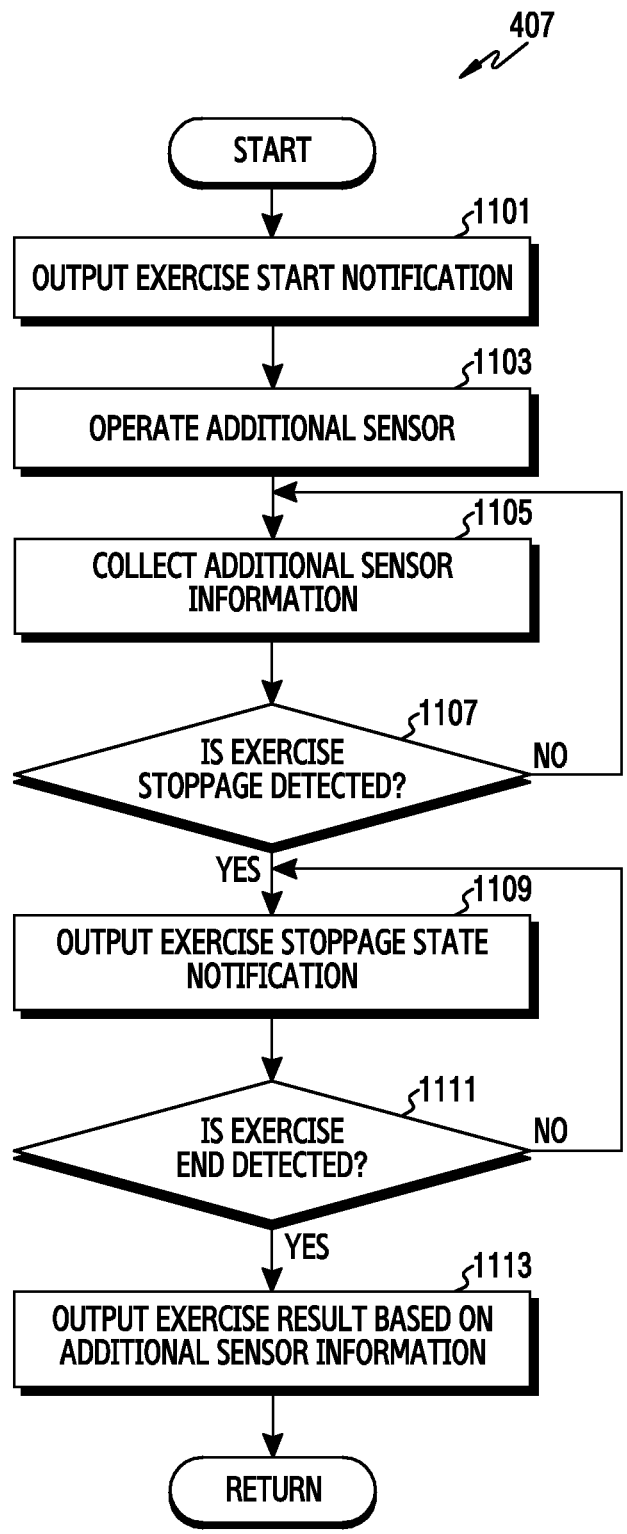
FIG. 11 is a flowchart of a method used by the electronic apparatus for outputting an exercise start notification, according to an embodiment of the present disclosure.

FIG. 11 is a flowchart of a method used by the electronic apparatus 101 for outputting an exercise start notification, according to an embodiment of the present disclosure.

The procedure for outputting the exercise start notification may of the same as operation 407 illustrated in FIG. 4.

Referring to FIG. 11, in operation 1101, the electronic apparatus 101 may output the exercise start notification. The electronic apparatus 101 may report that the activity of the user carrying the electronic apparatus 101 is maintained.

In operation 1103, the electronic apparatus 101 may operate at least one designated additional sensor when an exercise effect is detected. The additional sensor may include a biometric sensor (e.g., a heart rate sensor) and/or a position measurement sensor (e.g., a GPS). The additional sensor may include a sensor that collects sensor information associated with movement information (e.g., an accelerometer, a passometer, and a pedometer).

In operation 1105, the electronic apparatus 101 may collect sensor information from the at least one designated additional sensor.

In operation 1107, the electronic apparatus 101 may determine whether the exercise is stopped. A stoppage of the exercise may be a state in which the activity of the user carrying the electronic apparatus 101 is temporarily inactive. For instance, a stoppage of the exercise may be a state in which the user stops walking or running for a preset time (e.g., 1 minute) after starting a walking activity or running activity.

When a stoppage of the exercise is not detected in operation 1107, the electronic apparatus 101 may perform an operation of determining whether the exercise has stopped. For example, the electronic apparatus 101 may perform an operation associated with operation 1105.

When the stoppage of the exercise is detected in operation 1107, the electronic apparatus 101 may output an exercise stoppage state notification in operation 1109. For example, the electronic apparatus 101 may output the exercise stoppage state notification using visual, tactile, and audio notifications.

In operation 1111, the electronic apparatus 101 may determine whether the exercise is finished. The end of the exercise may be a state in which no additional activity is performed after stopping the activity of the user carrying the electronic apparatus 101. The end of the exercise may be a state in which a stoppage of the activity is maintained for a preset time (e.g., 5 minutes) or a state in which a user input to indicate the end of the exercise is detected with the stoppage of the activity detected.

When an end of the exercise is not detected in operation 1111, the electronic apparatus 101 may perform an operation of detecting whether the exercise is finished. The electronic apparatus 101 may perform an operation associated with operation 1109.

When the end of the exercise is detected in operation 1111, the electronic apparatus 101 may output an exercise result using sensor information in operation 1113. The electronic apparatus 101 may output an exercise result using sensor information collected from activity start time to exercise end time. The exercise result may include predetermined information (e.g., exercise type, exercise time, calorie consumption, moving speed, and average speed) that may be measured with sensor information associated with a movement, predetermined information (e.g., moving path) that may be measured with position measurement information, and predetermined information (e.g., heart rate) that may be measured with biometric information.

Figure 12:
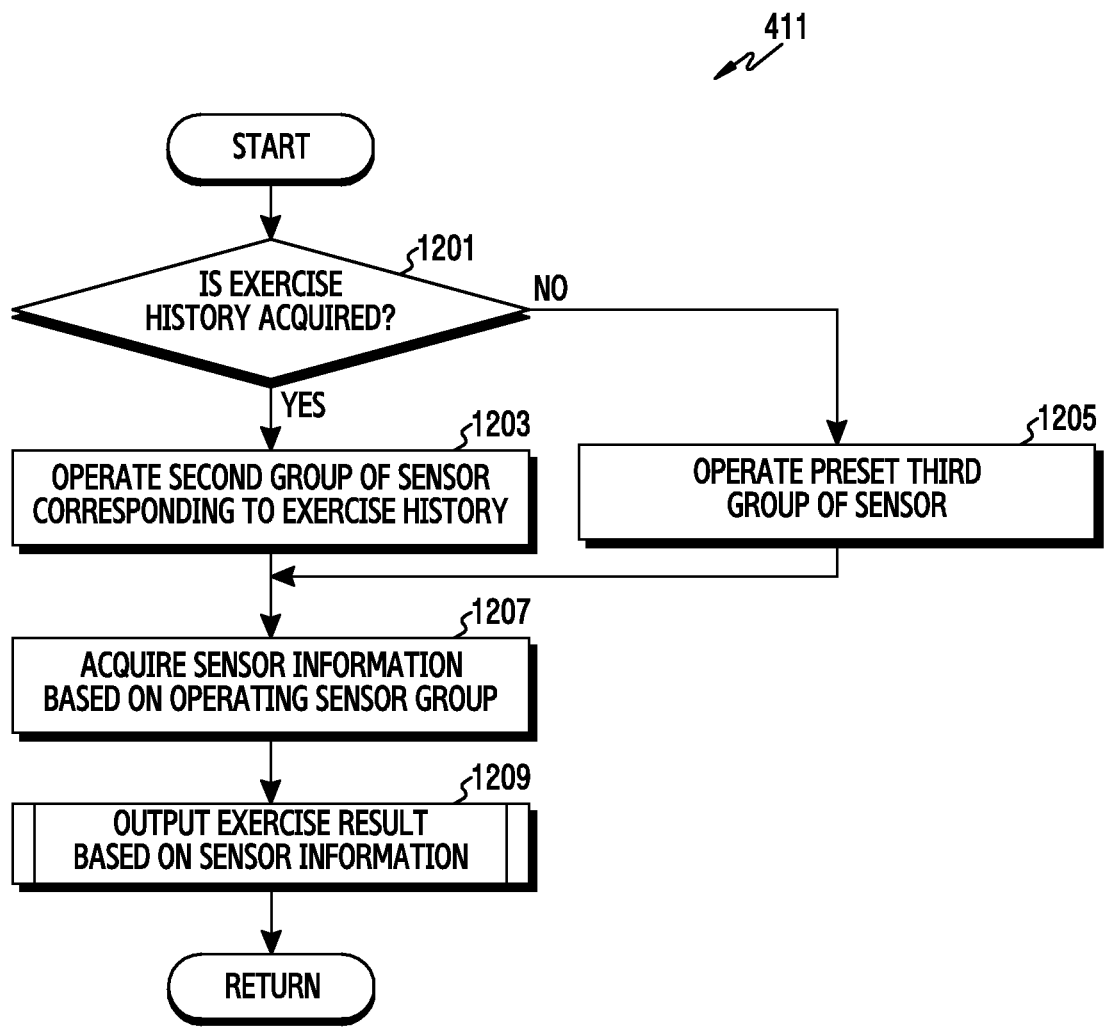
FIG. 12 is a flowchart of a method used by the electronic apparatus for entering an exercise mode, according to an embodiment of the present disclosure.

FIG. 12 is a flowchart of a method used by the electronic apparatus 101 for entering an exercise mode, according to an embodiment of the present disclosure. FIGS. 14A, 14B, 14C, and 14D are diagrams of an operation for outputting an exercise result, according to an embodiment of the present disclosure.

The procedure for entering the exercise mode may be the same as operation 411 illustrated in FIG. 4.

Figure 14A:
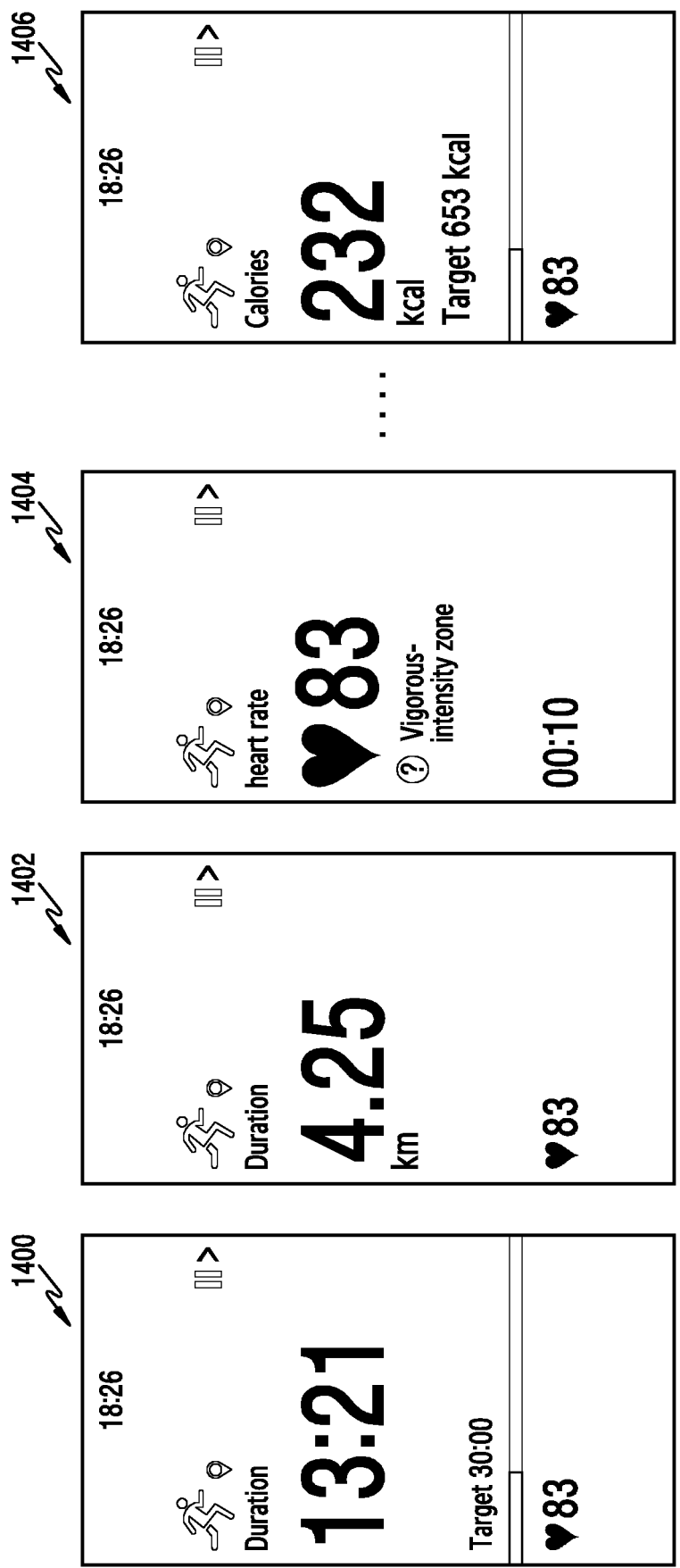
FIGS. 14A, 14B, 14C, and 14D are diagrams of an operation for outputting an exercise result, according to an embodiment of the present disclosure.

Referring to FIG. 12, in operation 1201, the electronic apparatus 101 may determine whether it is possible to acquire an exercise history from the electronic apparatus 101 or an external electronic apparatus. For example, the exercise history may be a record in a measurement mode implemented by the user carrying the electronic apparatus 101. For instance, as illustrated in FIG. 14A, the measurement mode may include at least one of an exercise time measurement mode 1400, an exercise distance measurement mode 1402, a biometric information measurement mode 1404, and a calorie measurement mode 1406.

When the exercise history is acquired in operation 1201, the electronic apparatus 101 may operate a second group of sensors corresponding to the exercise history in operation 1203. The second group of sensors may include some sensors installed in the electronic apparatus 101. When an exercise history of frequently using the biometric information measurement mode is obtained, the electronic apparatus 101 may operate a sensor capable of collecting biometric information.

When an exercise history is not acquired in operation 1201, the electronic apparatus 101 may operate a preset third group of sensors in operation 1205. The third group of sensors may include all sensors installed in the electronic apparatus 101.

In operation 1207, the electronic apparatus 101 may acquire sensor information based on an operating sensor group.

Figure 14B:
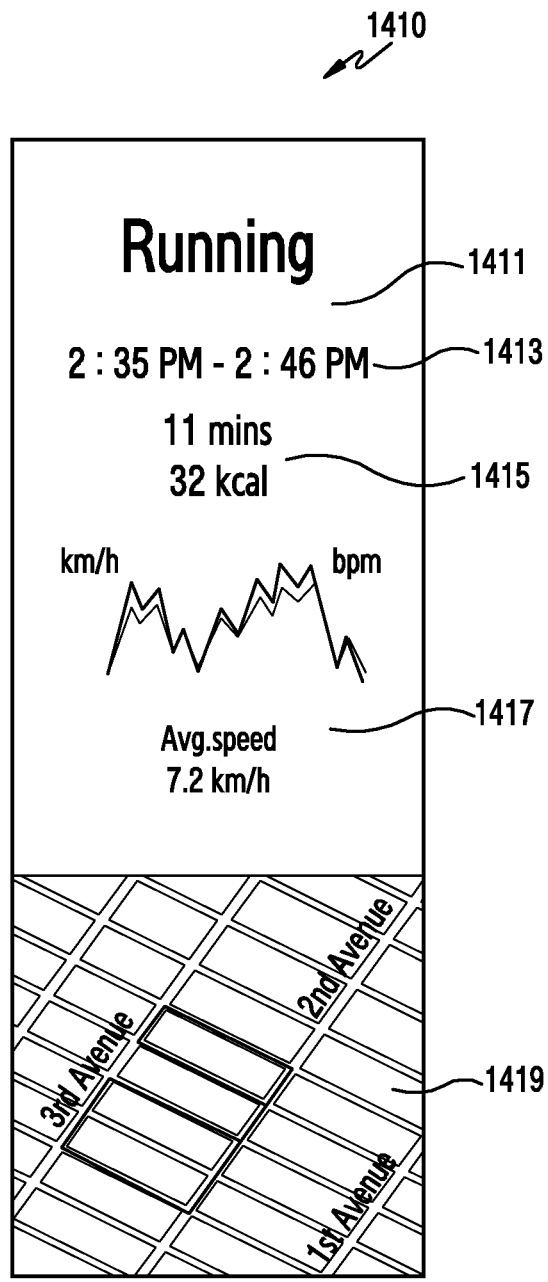

In operation 1209, the electronic apparatus 101 may output an exercise result based on the sensor information. The electronic apparatus 101 may output an exercise result using sensor information collected by the second group or the third group of sensors from activity start time to exercise end time. For instance, as illustrated in FIG. 14B, the exercise result 1410 may include predetermined information (e.g., exercise type 1411, exercise time 1413, calorie consumption 1415, moving speed, and average speed 1417) that may be measured with sensor information associated with a movement and predetermined information (e.g., moving path 1419) that may be measured with position measurement information.

Figure 14C:
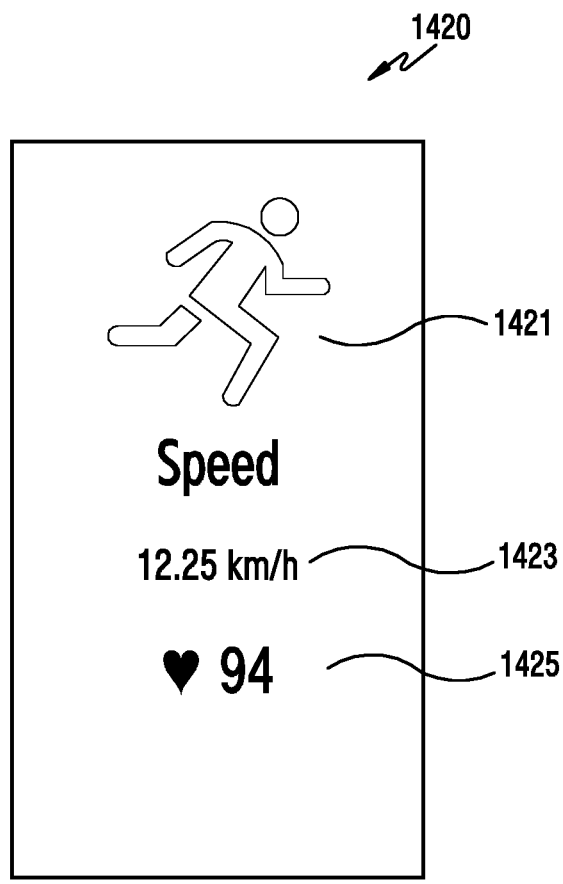

The electronic apparatus 101 may switch a currently output screen to another screen based on a preset input (e.g., right-left scrolling). For example, the electronic apparatus 101 may determine a measurement mode selected or designated by an input and may output an exercise result corresponding to the determined measurement mode. When a moving speed measurement mode is designated, the electronic apparatus 101 may output an exercise result 1420 including information 1421 indicating the moving speed measurement mode, moving speed 1423, and heart rate information 1425 according to moving speed, as illustrated in FIG. 14C.

The electronic apparatus 101 may acquire a target exercise amount in the measurement mode selected or designated by the input. For example, the target exercise amount may be designated by the user. The electronic apparatus 101 may determine whether a target is attained by comparing a current exercise amount with the target exercise amount. When a measured exercise amount exceeds the target exercise amount, the electronic apparatus 101 may determine that the target is attained.

Figure 14D:
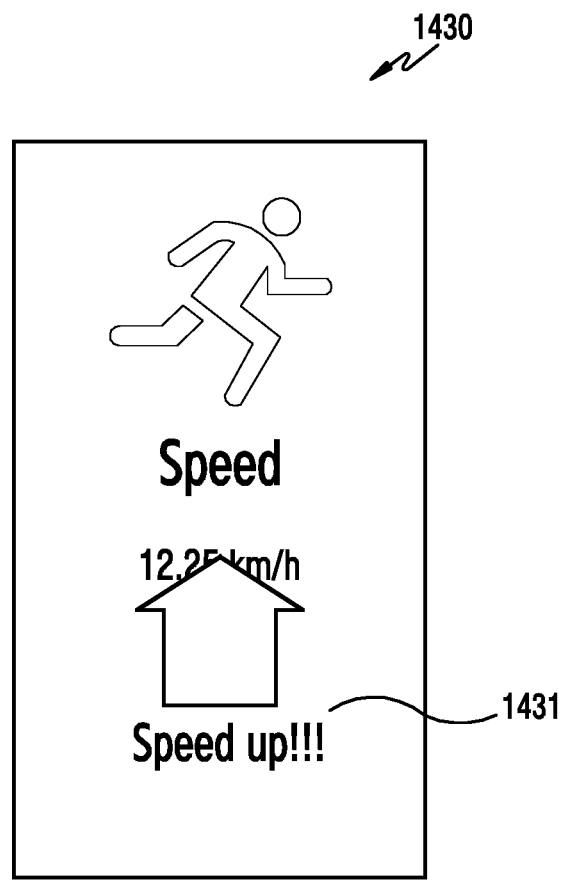

When it is determined whether the target is attained, the electronic apparatus 101 may output additional information corresponding to a determination result. The additional information may include information (e.g., a badge) indicating the attainment of the target. When the target is attained, the electronic apparatus 101 may compare a target attainment record with a previous attainment record or an attainment record of another user to assign an attainment ranking to the target attainment record. The additional information may include information on an exercise amount needed to attain the target. For instance, as illustrated in FIG. 14D, when the target is not attained, the electronic apparatus 101 may output 1430 information 1431 indicating that a speed increase is necessary to attain the target.

Figure 13:
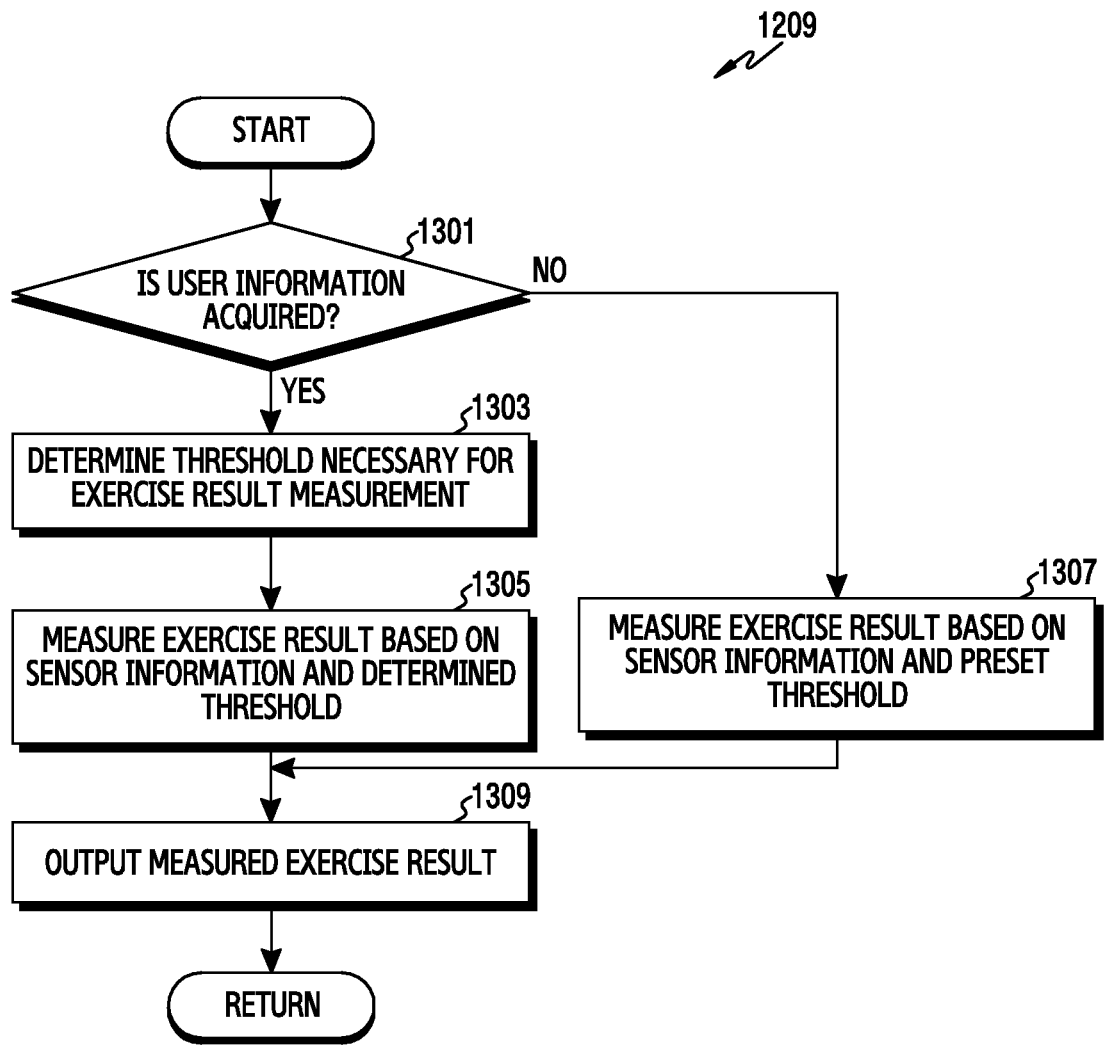
FIG. 13 is a flowchart of a method used by the electronic apparatus for outputting an exercise result, according to an embodiment of the present disclosure.

FIG. 13 is a flowchart of a method used by the electronic apparatus 101 for outputting an exercise result, according to an embodiment of the present disclosure.

The procedure for outputting the exercise result may be the same as operation 1209 illustrated in FIG. 12.

Referring to FIG. 13, the electronic apparatus 101 may measure an exercise result using a measurement threshold. The electronic apparatus 101 may use different measurement thresholds depending on user characteristics (e.g., age, gender, and body types).

In operation 1301, the electronic apparatus 101 may determine whether user information to determine user characteristics is acquired. When operating in an exercise result measurement mode, the electronic apparatus 101 may collect, as user information, at least one of profile information (e.g., name and age) on the user, activity history information (e.g., weekly activity amount and favorite activities), activity pattern information (e.g., activity period, inactivity period, and sleeping period), a biometric information measurement history (e.g., information on heart rate during activity), and a medical history.

When the user information is acquired in operation 1301, the electronic apparatus 101 may determine a measurement threshold corresponding to a user characteristic in operation 1303. The electronic apparatus 101 may determine a first measurement threshold for exercise result measurement when a male user is identified. The electronic apparatus 101 may determine a second measurement threshold for exercise result measurement when a female user is identified.

In operation 1305, the electronic apparatus 101 may measure an exercise result based on sensor information and the determined measurement threshold.

When user information is not acquired in operation 1301, the electronic apparatus 101 may measure an exercise result based on sensor information and a preset measurement threshold in operation 1307.

In operation 1309, the electronic apparatus 101 may output the measured exercise result through the display.

An operating method of an electronic apparatus may include: generating information indicating an activity start when first data indicating that an activity of the electronic apparatus occurs is received from a sensor; and generating information indicating an exercise start when second data indicating that the activity is converted into exercise is received from the sensor.

The method may further include measuring exercise information by detecting an exercise information measurement event after generating the information indicating the exercise start.

The generating of the information indicating the activity start may include outputting the information in a first size.

The generating of the information indicating the exercise start may include outputting the information in a second size that is larger than the first size.

The measuring of the exercise information may include: operating an additional sensor different from the sensor; and measuring exercise information based on data received from the sensor and the additional sensor.

The generating of the information indicating the exercise start may include measuring exercise information based on at least part of data received from the sensor.

The measuring of the exercise information may include changing a threshold for measuring the exercise information based on a characteristic of a user.

An electronic apparatus and an operating method thereof may provide an exercise information measurement function that detects a movement with a pattern based on sensor information to output predetermined information, thus enabling a user to recognize the start of a specified activity. In addition, various exemplary embodiments may provide an exercise information measurement function that outputs whether a started activity has exercise effects, thereby motivating the user to exercise and helping the user to develop healthy habit.

While the present disclosure has been shown and described with reference to certain embodiments thereof, it will be understood by those skilled in the art that various changes in form and details may be made therein without departing from the scope of the present disclosure. Therefore, the scope of the present disclosure should not be defined as being limited to the embodiments, but should be defined by the appended claims and equivalents thereof.

What is claimed is:

1. An electronic apparatus comprising:
a display;
a sensor group including a first sensor and a plurality of second sensors; and
at least one processor connected to the display and the sensor group,
wherein the at least one processor is configured to:
display, via the display, a first user interface (UI) indicating a start of an activity when first data indicating that the activity of the electronic apparatus occurs is received from the first sensor,
display, via the display, information about a preset time required for the activity to be converted into exercise, wherein the preset time is set based on user information related to a characteristic of a user,
detect that the activity is maintained for the preset time, based on a detected pattern of the activity of the electronic apparatus via the first sensor,
in response to the detecting, display a second UI indicating a start of the exercise via the display,
activate at least one sensor from among the plurality of second sensors based on the start of the exercise and exercise history of the user, and
execute a function for measuring exercise information by using second data received from the activated at least one sensor.

2. The electronic apparatus of claim 1, further comprising a memory configured to store information for measuring the exercise information,
wherein the information for measuring the exercise information includes a pattern threshold for determining meaningful activity based on a pattern detected via the first sensor, a threshold for determining whether a detected activity is converted into exercise, and a threshold for determining whether an activity determined to be converted into exercise has stopped or finished.

3. The electronic apparatus of claim 1, further comprising communication circuitry,
wherein the user information includes medical history information, and
wherein the electronic device acquires the user information from an external electronic apparatus via the communication circuitry.

4. The electronic apparatus of claim 1, wherein the at least one processor is further configured to change a threshold for measuring the exercise information based on the characteristic of the user.

5. The electronic apparatus of claim 1, wherein the at least one processor is further configured to display a menu for determining whether to execute the function, and execute the function based on an input on the displayed menu.

6. The electronic apparatus of claim 1, wherein the at least one processor is further configured to display a screen indicating an activity of the user on the display and display the first UI on a first area of the screen based on the first data.

7. The electronic apparatus of claim 6, wherein the at least one processor is further configured to display the second UI in a second area, which is larger than the first area, of the screen based on the second data.

8. The electronic apparatus of claim 1, wherein the at least one processor is further configured to display the measured exercise information on the display.

9. The electronic apparatus of claim 1, wherein the at least one processor is further configured to display a third UI indicating that the exercise has stopped when third data indicating that the activity has stopped is received from the sensor group, after displaying the first UI.

10. The electronic apparatus of claim 1, wherein the at least one processor is further configured to display a fourth UI including the measured exercise information when fourth data indicating that the activity has ended is received from the sensor group, after displaying the first UI.

11. The electronic apparatus of claim 1, wherein the at least one processor is further configured to output guide information based on the measured exercise information and a preset target exercise amount.

12. The electronic apparatus of claim 1, wherein the first sensor comprises a pedometer, and a second sensor comprises a biometric sensor.

13. A method of an electronic apparatus including a sensor group, the method comprising:
displaying a first user interface (UI) indicating a start of an activity when first data indicating that the activity of the electronic apparatus occurs is received from a first sensor of the sensor group;

display information about a preset time required for the activity to be converted into exercise, wherein the preset time is set based on user information related to a characteristic of a user;

detecting that the activity is maintained for the preset time, based on a detected pattern of the activity of the electronic apparatus via the first sensor;

in response to the detecting, by the electronic apparatus, that the activity is maintained for at least one of the preset time or at the preset intensity, displaying a second UI indicating a start of an exercise;

activating at least one sensor from among a plurality of second sensors in the sensor group based on the start of the exercise and exercise history of the user; and executing a function for measuring exercise information by using second data received from the activated at least one sensor.

14. The method of claim 13, further comprising:
identifying information for measuring the exercise information,
wherein the information for measuring the exercise information includes a pattern threshold for determining meaningful activity based on a pattern detected via the first sensor, a threshold for determining whether a detected activity is converted into exercise, and a threshold for determining whether an activity determined to be converted into exercise has stopped or finished.

15. The method of claim 13, the method further comprising:
wirelessly receiving, from an external electronic device, the user information,
wherein the user information includes medical history information.

16. The method of claim 13, wherein measuring the exercise information comprises changing a threshold for measuring the exercise information based on the characteristic of the user.

17. The method of claim 13, wherein executing the function comprises:
displaying a menu for determining whether to execute the function; and
executing the function based on an input on the displayed menu.

18. The method of claim 13, wherein the first UI is displayed on a first area of a screen indicating an activity of the user, and the second UI is displayed on a second area, which is larger than the first area, of the screen.

19. The method of claim 13, the method further comprising:
displaying the measured exercise information on a display of the electronic apparatus.

20. A non-transitory computer-readable recording medium that stores a program in a memory of an electronic device, the program when executed performing a method comprising:
displaying a first user interface (UI) indicating a start of an activity when first data indicating that the activity of the electronic apparatus occurs is received from a first sensor among a sensor group in the electronic device;
displaying information about a preset time required for the activity to be converted into exercise, wherein the preset time is set based on user information related to a characteristic of a user;
detecting that the activity is maintained for the preset time, based on a detected pattern of the activity of the electronic apparatus via the first sensor;
in response to the detecting, displaying a second UI indicating a start of the exercise;
activating at least one sensor from among a plurality of second sensors in the sensor group based on the start of the exercise and exercise history of the user; and
executing a function for measuring exercise information by using second data received from the activated at least one sensor.

* * * * *